United States Patent [19]
Rose et al.

[11] Patent Number: 5,932,806
[45] Date of Patent: *Aug. 3, 1999

[54] CONTAMINANT DETECTION SYSTEM

[75] Inventors: Joseph Lawrence Rose, State College, Pa.; Aleksander Boleslaw Pilarski, deceased, late of State College, Pa., by Jadwiga Pilarska, Piotr Pilarski; Jeffrey Mark Hammer, Wayzata, Minn.; Michael Todd Peterson, Lakeville, Minn.; Philip Otto Readio, Savage, Minn.

[73] Assignee: The B.F. Goodrich Company, Akron, Ohio

[ * ] Notice: This patent is subject to a terminal disclaimer.

[21] Appl. No.: 08/853,265

[22] Filed: May 9, 1997

Related U.S. Application Data

[63] Continuation of application No. 08/355,357, Dec. 13, 1994, Pat. No. 5,629,485.

[51] Int. Cl.⁶ .................................................. G01N 29/00
[52] U.S. Cl. .......................................... 73/599; 73/170.26
[58] Field of Search .................................. 340/580, 582, 340/962; 364/563; 244/134 F; 367/13; 73/170.26, 579, 583, 599, 627

[56] References Cited

U.S. PATENT DOCUMENTS

| | | | |
|---|---|---|---|
| 3,836,846 | 9/1974 | Overall | 340/580 |
| 4,308,751 | 1/1982 | Thurner | 73/627 |
| 4,335,613 | 6/1982 | Luukkala | 73/599 |
| 4,461,178 | 7/1984 | Chamuel | 340/582 |
| 4,470,123 | 9/1984 | Magenheim | 340/580 |
| 4,570,881 | 2/1986 | Lustenberger | 244/134 F |
| 4,604,612 | 8/1986 | Watkins et al. | 73/599 |
| 4,628,736 | 12/1986 | Kirby et al. | 73/590 |
| 4,674,334 | 6/1987 | Chimenti et al. | 73/627 |
| 4,833,660 | 5/1989 | Deom et al. | 367/157 |
| 4,891,628 | 1/1990 | Zuckerman | 340/582 |
| 5,005,015 | 4/1991 | Dehn | 340/580 |
| 5,014,042 | 5/1991 | Michoud et al. | 340/583 |
| 5,095,754 | 3/1992 | Hsu et al. | 73/602 |
| 5,187,980 | 2/1993 | Blair et al. | 73/599 |
| 5,195,046 | 3/1993 | Gerardi et al. | 364/506 |
| 5,467,944 | 11/1995 | Luukkala | 244/134 F |
| 5,474,261 | 12/1995 | Stolarczyk et al. | 244/134 F |
| 5,507,183 | 4/1996 | Larue et al. | 73/598 |

FOREIGN PATENT DOCUMENTS

| | | |
|---|---|---|
| 0 619 488 | 10/1994 | European Pat. Off. . |
| 2 695 373 | 3/1994 | France . |
| 2 217 962 | 10/1973 | Germany . |
| 1117664 | 6/1968 | United Kingdom . |
| 1 433 832 | 4/1976 | United Kingdom . |

OTHER PUBLICATIONS

Carlin, B. Ultrasonics. N.Y., McGraw–Hill Book Company, Inc., 1949. pp. 40–43. (no month).

"Ultrasonic System Measures Elastic Properties of Composites", NASA Tech Brief vol. 17, No. 11, Item #7 from JPL New Technology Report NPO–18729, Nov. 1993.

"Visualization of Lamb Mode patterns In A Glass Plate", Ultrasonics 1994 vol. 32 No. 4.

"Surface and Plate Waves In Layered Structures", 1988, The American Society for Nondestrictive Testing, Inc., Materials Evaluation/46/Apr. 1988.

"Lamb Wave Mode Selection Concepts for Interfacial Weakness Analysis", Journal of Nondestructive Evaluation, vol. 11, Nos. 314, 1992.

"Health Monitoring System for Aircraft", Presented at the Active materials & Adaptive Structures Conf. '91., VA.

*Primary Examiner*—Christine K. Oda
*Attorney, Agent, or Firm*—Westman, Champlin & Kelly, P.A.

[57] ABSTRACT

A contaminant detection system includes a transmitter for transmitting a guided wave through the skin at particular resonances, wherein each resonance point utilized will have propagation characteristics sensitive to a condition of interest. A contaminant may then be classified by transmitting several resonances and then carrying out appropriate feature extraction and pattern recognition techniques utilizing a host processor.

19 Claims, 23 Drawing Sheets

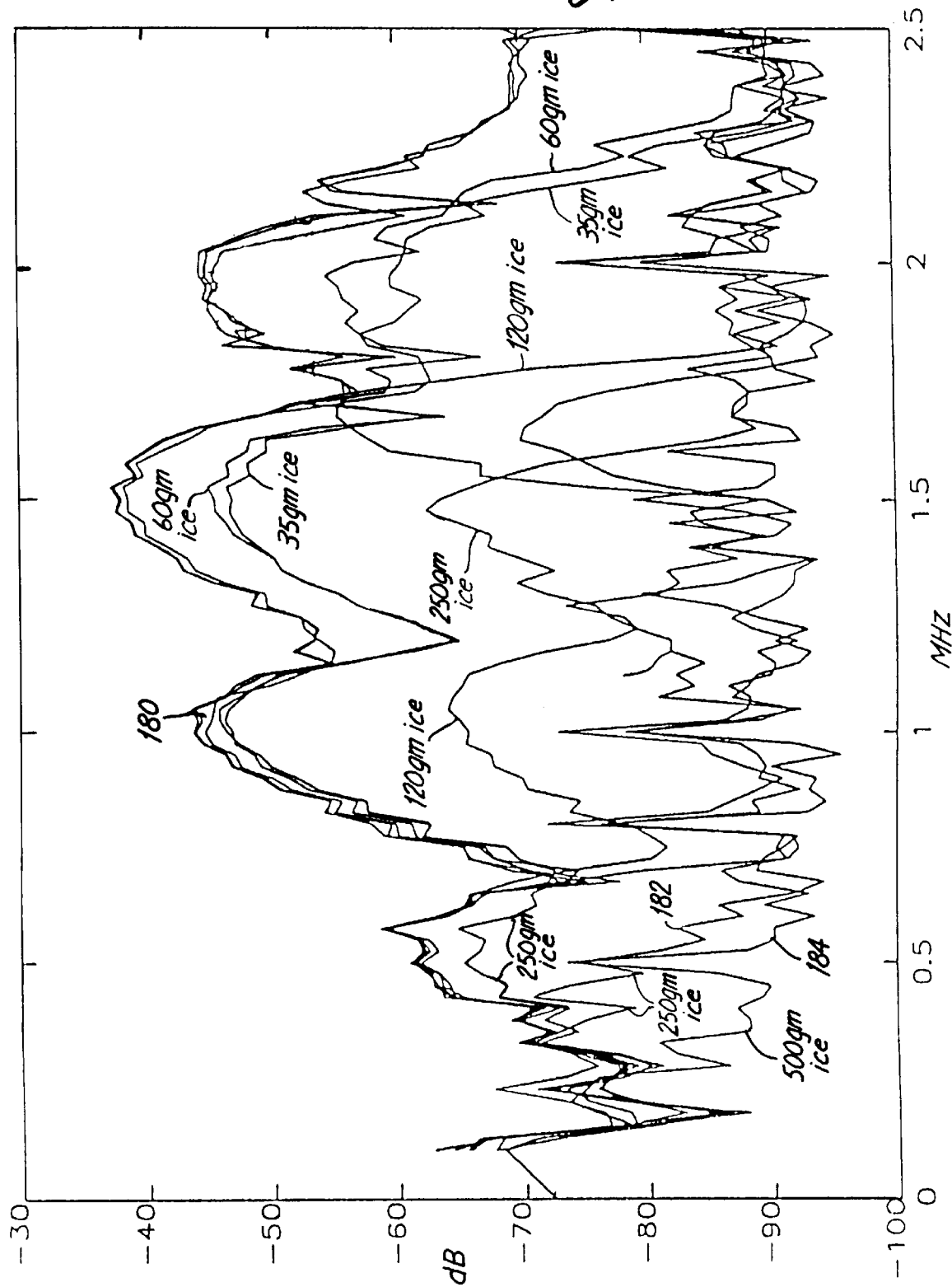

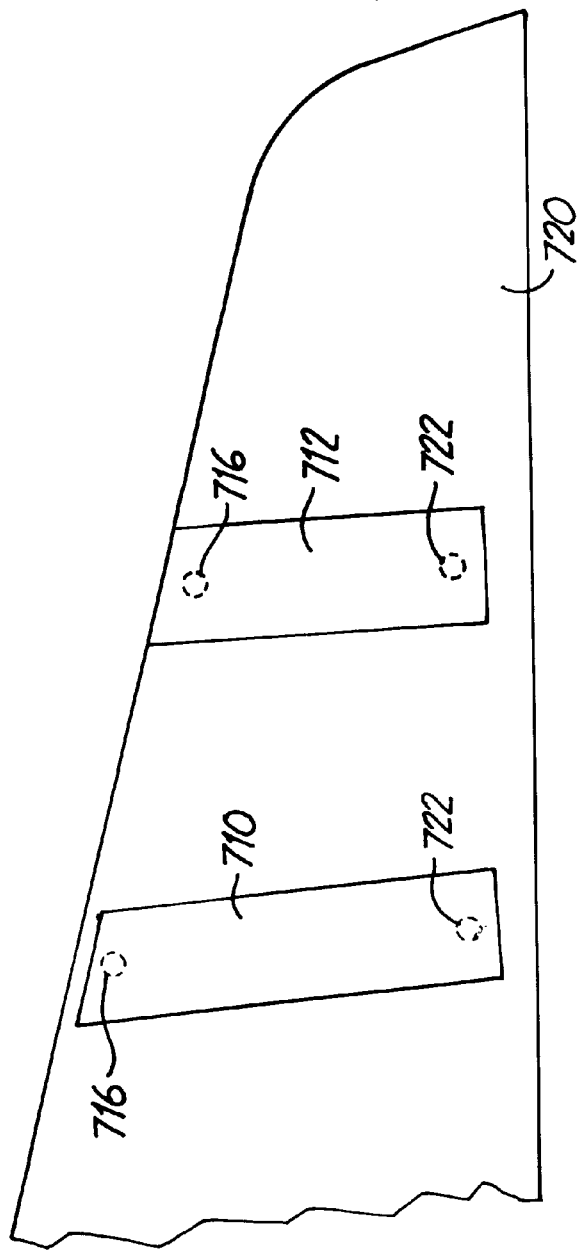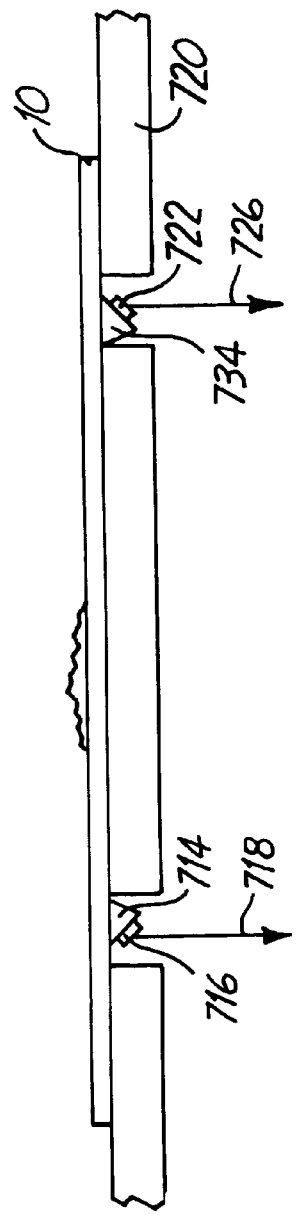

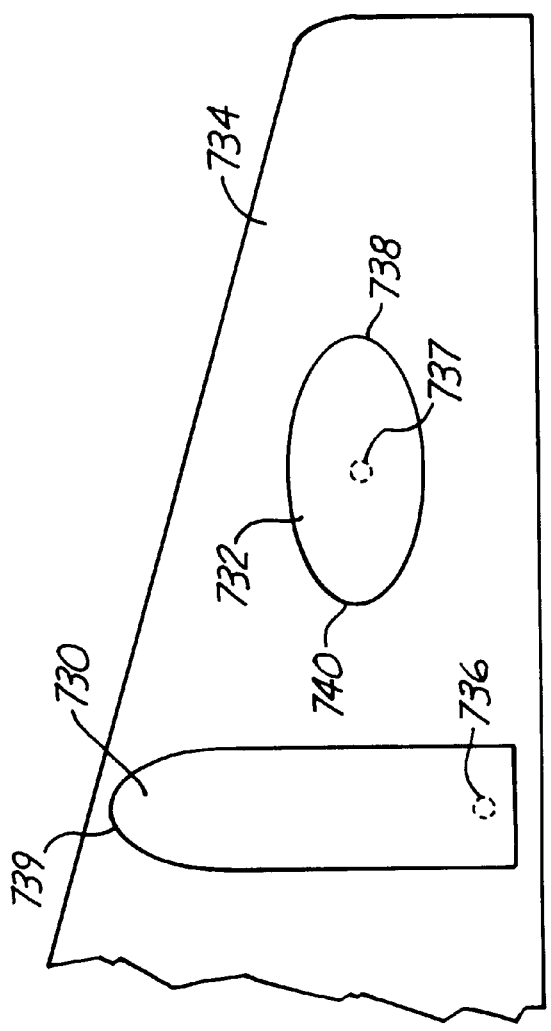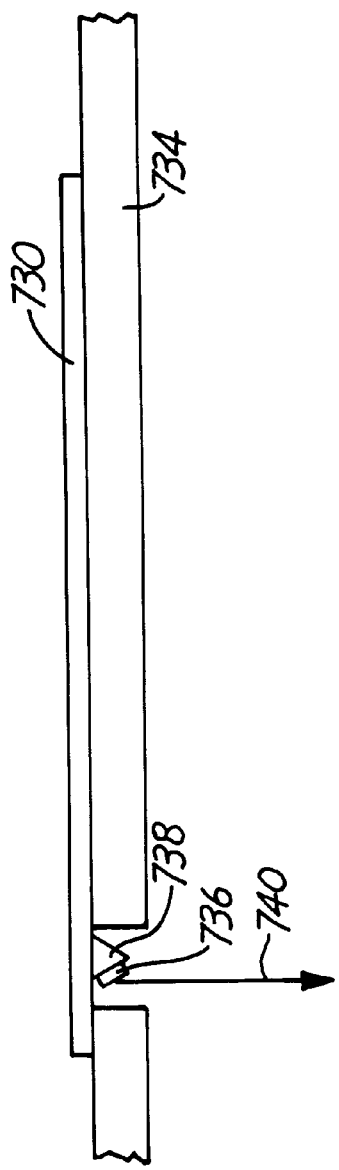

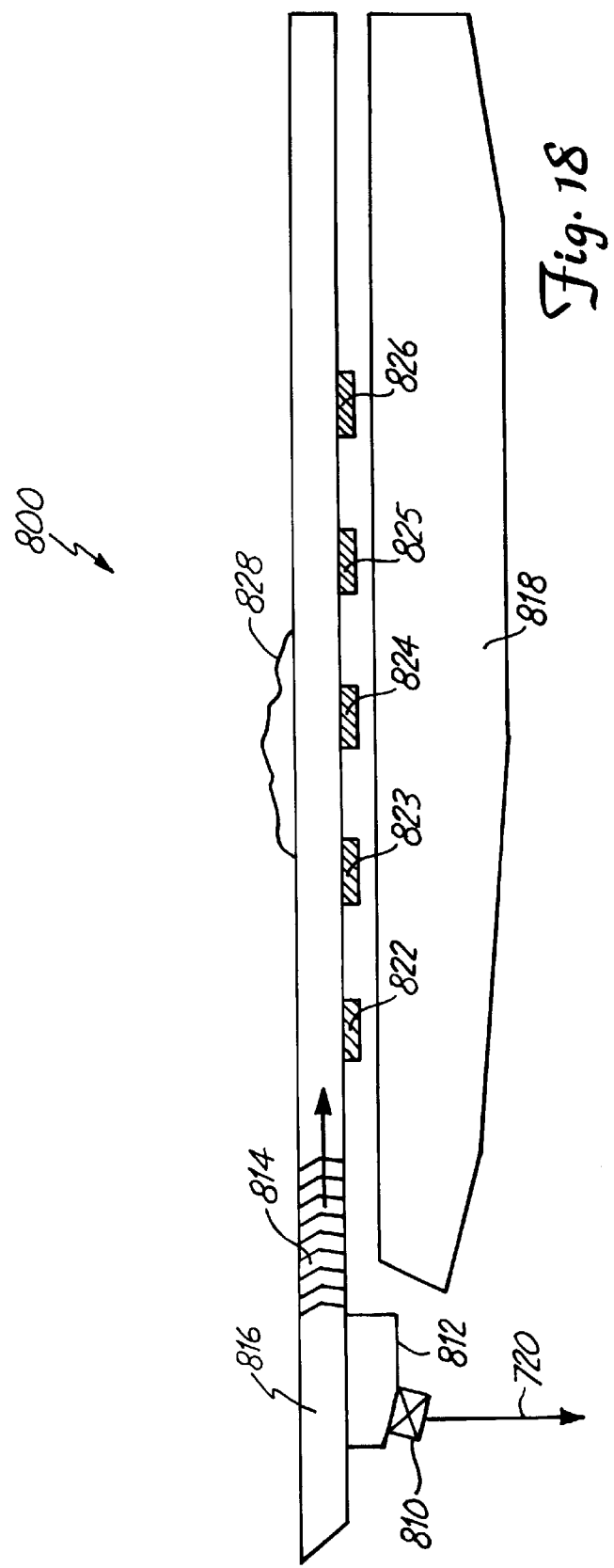

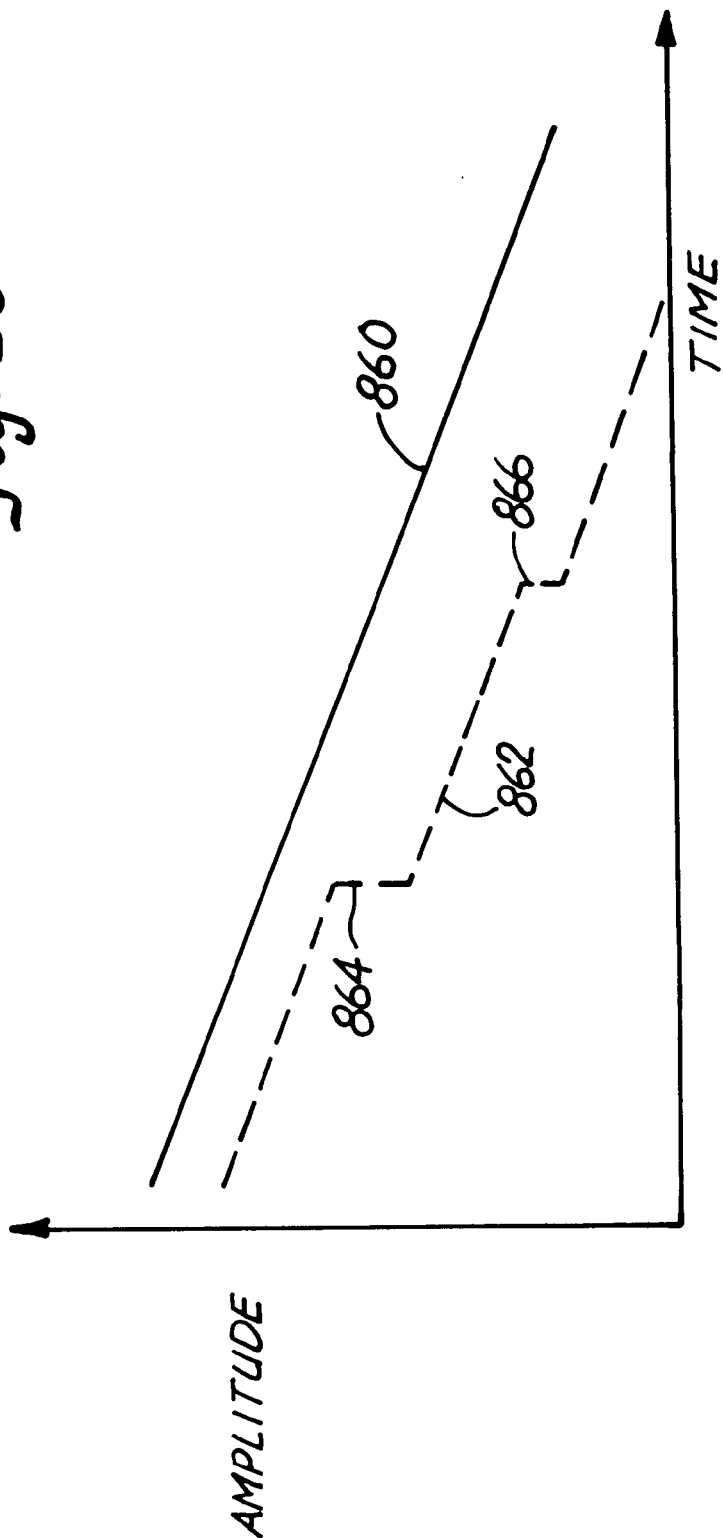

5,932,806

CONTAMINANT DETECTION SYSTEM

This is a continuation of application Ser. No. 08/355,357, filed Dec. 13, 1994, U.S. Pat. No. 5,629,485. Priority of the prior application is claimed pursuant to 35 USC §120.

TECHNICAL FIELD

The present invention relates to contaminant detectors, and more particularly, to devices for detecting and classifying contaminants on aircraft surfaces utilizing differently polarized guided waves that achieve multiple resonances on dispersion curves.

BACKGROUND OF THE INVENTION

Under certain operating conditions, aircraft are vulnerable to the accumulation of contaminants on external component surfaces or skins. Examples of such contaminants include ice, water, glycol, oils and fuel. If left unchecked, the accumulation of certain contaminants, and in particular ice, can eventually so laden the aircraft with additional weight and so alter airfoil configuration as to cause undesirable flying conditions. The ability to detect the accumulation of contaminants on such surfaces, and the ability to classify those contaminants so as to identify dangerous flight conditions, has therefore become highly desirable.

A number of different kinds of contaminant detectors have been utilized for such objectives. Among these types are ultrasonic contaminant detectors, which utilize ultrasonic energy transmitted through an aircraft or airfoil skin.

One such ultrasonic ice detector is described in U.S. Pat. No. 4,461,178 issued to Jacques R. Chamuel (Chamuel). In Chamuel, an ultrasonic signal generator applies an output to a transducer which converts the signal energy into an ultrasonic wave which is passed through a portion of the airfoil skin and is sensed by a second transducer. The waveform transmitted includes a compressional portion and a flexural portion. The compressional portion and a flexural portion. The receiving transducer receives an initial waveform which corresponds to the compressional wave transmitted through the airfoil skin from the source transducer. Subsequent to the compressional wave, a larger spike corresponds to the first receipt of the flexural wave transmitted through the airfoil skin. A layer of ice on the surface of the airfoil will affect the signal waveforms, wherein the flexural wave component will be attenuated while the compressional waveform remains basically unchanged. The ratio of the peak magnitudes of the received compressional and flexural wave portions provides an indication corresponding to ice accumulation.

Control of the transmitted signal into a specific mode and waveform shape is difficult when using the normal beam excitation transducer of Chamuel, because these type of transducers have a tendency to produce higher phase velocity signals closer to cut-off frequency. Differentiating between ice and water is therefore difficult utilizing the Chamuel system. As mentioned before, it is desirable to have the ability to distinguish between ice and water because accumulated ice is dangerous for flying while accumulated water is not.

Another ultrasonic ice detector is described in U.S. Pat. No. 4,604,612 issued to Watkins, et al. Watkins, et al. also utilizes a transmitting and receiving transducer, wherein the transmitter transmits pulses of horizontal polarized shear waves which propagate through the airfoil skin with a wavelength comparable to the thickness of the sheet so that the shear waves are guided by the surface. If the surface is dry, or covered in water (in which horizontally polarized shear waves cannot propagate) the received pulses will have a larger amplitude than if the surface is covered by a layer of ice in which shear waves can propagate. This is because some of the energy of the shear wave pulse will be dissipated due to propagation through the ice. Consequently, the Watkins, et al. ice detector can detect ice adhering to the surface but is insensitive to the presence of water.

Much like Chamuel, it is therefore impossible to detect a layer of ice covering a thin layer of water with the teachings of Watkins, et al. Ice on water is also a dangerous condition for flying.

An ultrasonic system which can reliably identify and distinguish between the build-up of various forms of airfoil contaminants, particularly between the formation of water and ice is therefore highly desirable.

DISCLOSURE OF THE INVENTION

An object of the present invention is to provide an ultrasonic contaminant detection system which discriminates between various contaminant types.

According to one aspect of the present invention, a contaminant detection system comprises:

a transmitter for transmitting: a) a first guided wave through the skin, said first guided wave having a first phase velocity and a first frequency; and b) a second guided wave through the skin, said second guided wave having a second phase velocity and a second frequency;

a receiver for receiving said first and second guided waves and providing first and second received signals indicative of the received first and second guided waves;

a signal processor for comparing said first and second received signals.

According to another aspect of the present invention, a method for detecting contaminants on an airfoil comprises the steps of:

transmitting a first guided wave through the skin, said first guided wave having a first phase velocity and a first frequency;

receiving said first guided wave and providing a first received signal indicative thereof;

transmitting a second guided wave through the skin, said second guided wave having a second phase velocity and a second frequency;

receiving said second guided wave and providing a second received signal indicative thereof;

comparing said first received signal with said second received signal.

According to another aspect of the present invention, a method of detecting contaminants on a skin comprises the steps of:

transmitting a guided wave containing multiple resonances through the skin;

receiving the transmitted signal and providing a received signal indicative thereof; and, extracting features from the frequency signature of said received signal for classifying contaminants on the skin.

According to another aspect of the present invention, a contaminant detection system comprises:

a transmitter for transmitting: a) a first guided wave through the skin, said first guided wave having a first phase velocity and a first frequency; and b) a second guided wave through the skin, said second guided wave having a second phase velocity and a second frequency;

a receiver for receiving said first and second guided waves and providing first and second received signals indicative of the received first and second guided waves;

a signal processor for comparing said first and second received signals; and, a coupler for providing said transmitter with predetermined angles of incidence.

The present invention utilizes special transmission resonance points in order to achieve multiple class contaminant discrimination. It obtains superior penetration power and therefore has improved sensitivity to various contaminant states. In addition, the present invention can be conveniently packaged, is easily manufacturable, and easily serviceable.

These and other objects, features and advantages of the present invention will become more apparent in the light of the detailed description of exemplary embodiments thereof as illustrated by the drawings.

BRIEF DESCRIPTION OF THE DRAWINGS

FIG. 6c is a graph of amplitude vs. frequency of a received signal from a guided wave transmitted through a 0.087 inch thick aluminum plate with ice contaminant.

FIG. 13b is a side view of the transducer and coupler illustrated in FIG. 13a.

FIG. 15a is a top view of an alternative embodiment of a contaminant detection system in accordance with the present invention.

FIG. 15b is a side view of the contaminant detection system illustrated in FIG. 15a.

FIG. 16a is a top view of an alternative embodiment of a contaminant detection system in accordance with the present invention.

FIG. 16b is a side view of the contaminant detection system illustrated in FIG. 16a.

FIG. 18 is a side view of an alternative embodiment of a contaminant detection system in accordance with the present invention.

FIG. 20 is a graph illustrating amplitude versus time of a received signal for the contaminant detection system illustrated in FIGS. 18 and 19.

BEST MODE FOR CARRYING OUT THE INVENTION

Figure 1:
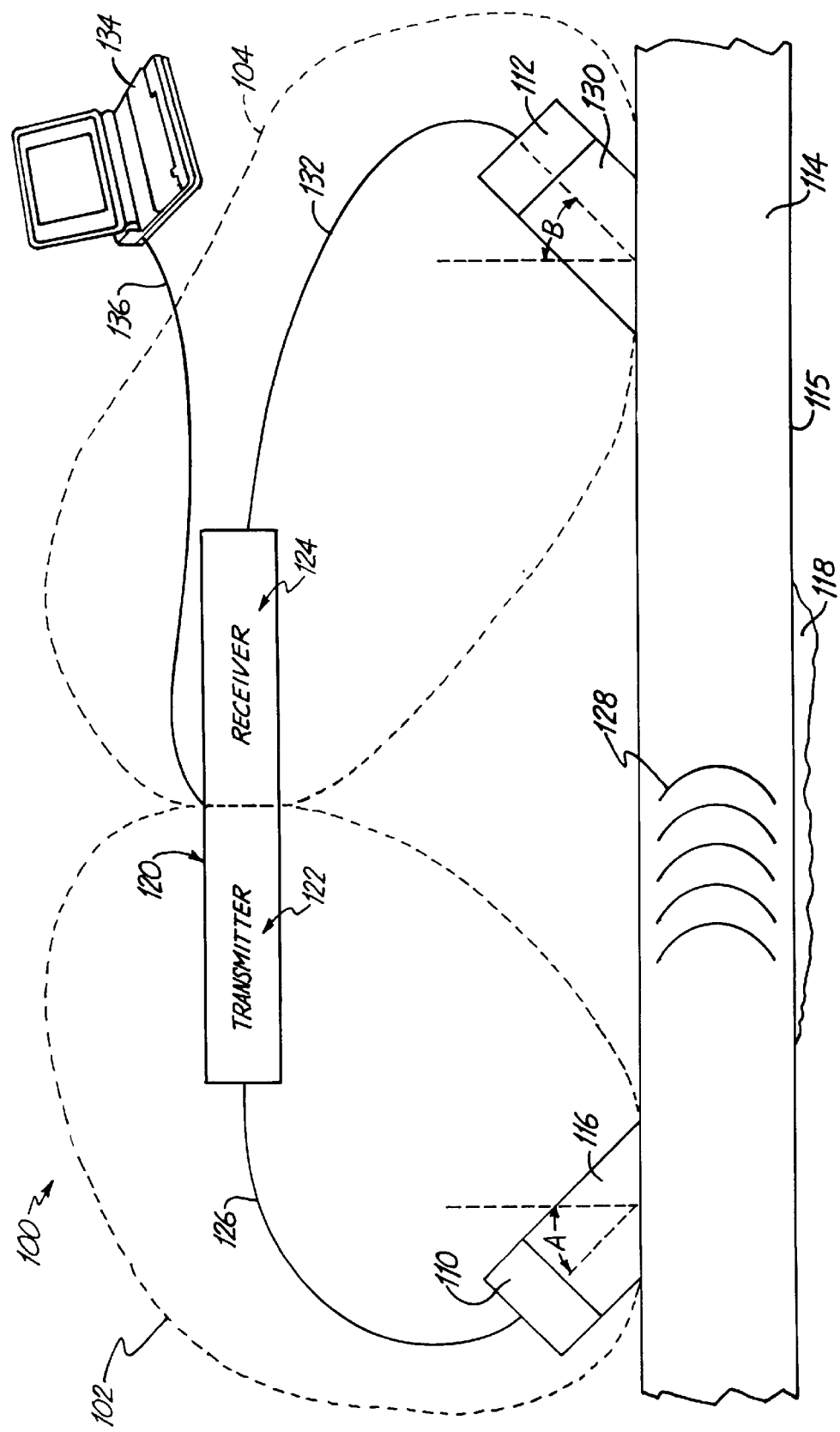
FIG. 1 is a schematic block diagram of a contaminant detection system in accordance with the present invention.

Referring now to FIG. 1, a contaminant detection system 100 in accordance with the present invention includes a transmitter section 102 and a receiver section 104. Transmitter section 102 transmits ultrasonic guided waves (represented by wave packet 128) through a skin 114, having an exposed surface 115 on which contaminants 118 accumulate. Often used terms for guided waves include plate, Lamb, symmetrical, compressional, anti-symmetrical, and flexural waves.

Skin 114 may be any type of structure which is exposed to the environment. For the purpose of the present invention, skin 114 is typically the outer shell of an airfoil. However, skin 114 may also be part of any of a number of other structures exposed to contaminants. Skin 114 is preferably comprised of a material which has favorable ultrasonic transmission characteristics, such as metals like aluminum (Al) or titanium (Ti). It is to be noted, though, that other materials, including composites may be utilized.

Transmitter section 102 includes a transmitting ultrasonic waveform transducer or probe 110 which converts electrical energy to ultrasonic energy. A transmitter circuit 122 provides electric signal on a line 126 to probe 110. Probe 110 is acoustically coupled to skin 114 via a coupler or coupling wedge 116 which aligns the probe at an incident angle A. Angle A is picked so that the ultrasonic wave transmitted through skin 114 achieves a particular phase velocity value corresponding to multiple resonances or resonance points along a dispersion curve as frequency is swept.

Transducers 110, 112 may be any of a number of ultrasonic probes known in the art, such as piezoelectric probe model no. SWS8 available from Krautkramer Branson. The diameter of the transmitting transducer 110 should be at least twice the thickness of the skin and preferably at least three times. The bandwidth of the transducer should be as broad as possible so that a narrow band excitation function could be swept over a large frequency range.

Receiving section 104 includes a receiving transducer or probe 112 for converting the ultrasonic transmitted signal to a corresponding received electrical signal provided on a line 132. Probe 112 is acoustically coupled to skin 114 by a coupling wedge 130 which aligns the probe at an incident angle B. Angle B is determined as a function of many factors, such as skin thickness, etc. For a skin of constant thickness, angle B should be approximately equal to the transmit probe incident angle A.

A signal processor 120 includes a transmitter circuit 122 and a receiver circuit 124. Transmitter circuit 122 provides the electrical transmit signal on line 126. The electrical received signal on line 132 is provided to receiver circuit 124. Signal processor 120 is connected by a line 136 to a host controller or processor 134. Host controller 134 controls the transmit circuit 122 to provide specific transmit signals and receives, stores, manipulates and interprets the digitized received data. The host controller may be any of a number of computers well known to those skilled in the art. It is to be noted that the signal processor 120 may be comprised of multiple units rather than a singular unit as illustrated.

Couplers 116, 130 may be comprised of any of a number of suitable ultrasonic transmission materials, such as polymethyl methacrylate or other acrylic polymer.

Figure 2:
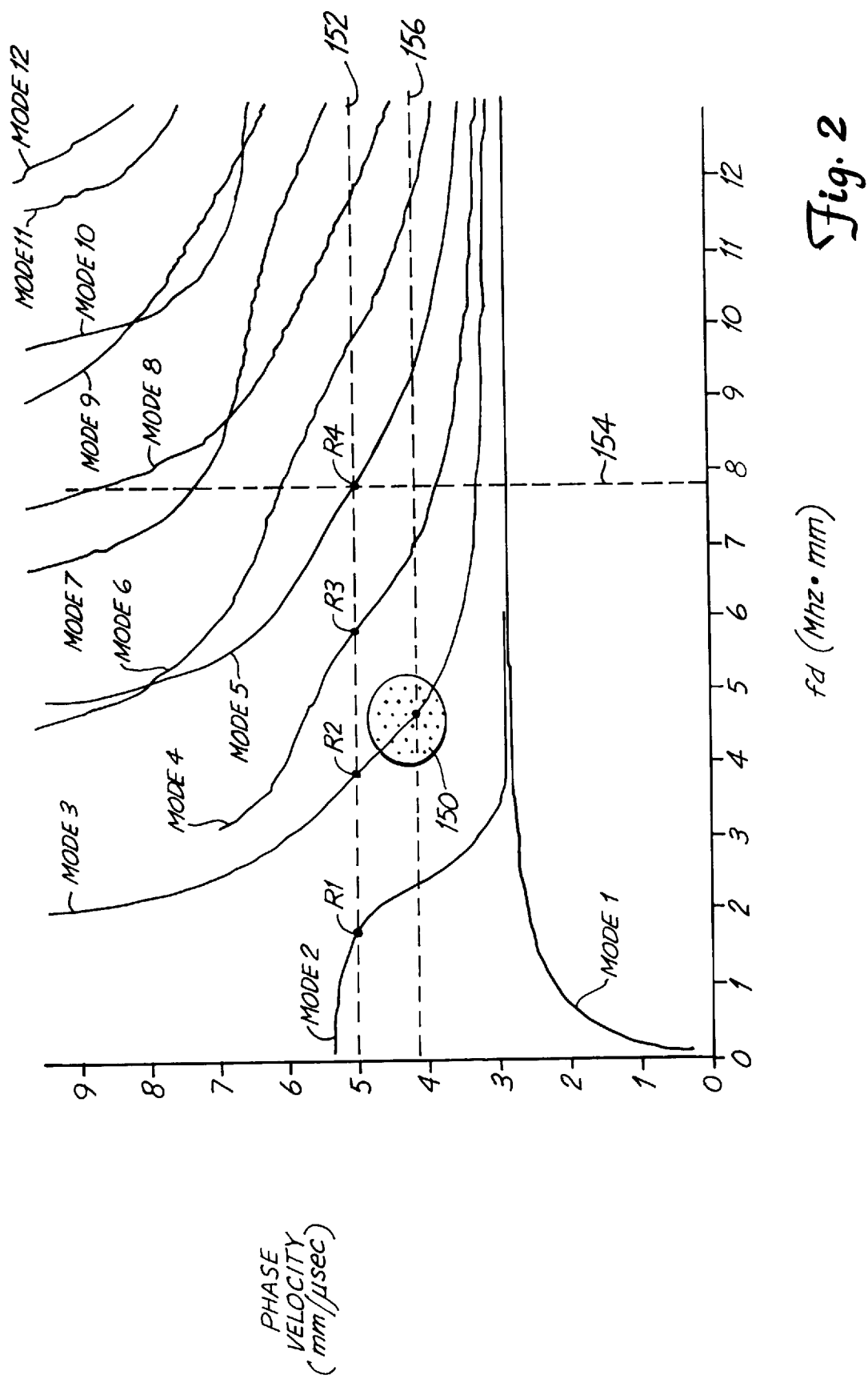
FIG. 2 is a graph of a dispersion curve showing phase velocity vs. frequencythickness product for transmission of guided waves through a metal skin.

Referring now to FIG. 2, the multimode character of guided waves and the various wave velocity values are shown in a "dispersion curve". Guided waves are highly dispersive elastic waves propagating along the skin and have many vibrational resonance points. Dispersion curves represent the natural resonances (or wave propagation states) that are allowed to propagate in a structure. Each curve or "mode" illustrated in the dispersion curve represents a natural resonance or wave propagation state. Twelve different wave propagation modes (Modes 1–12) in a metal skin for a particular wave length or frequency times thickness (fd) value are shown.

The incident angle A (see FIG. 1) of the transmission probe is functionally related to wave phase velocity. A fixed transmission probe incident angle therefore sets a specific phase velocity value and is illustrated as a horizontal line on the dispersion curve. A pair of horizontal lines 152, 156 are illustrative of points on the curves of two different incident angles. Line 152 is representative of a lower incident angle than that of line 156.

A vertical line 154 is illustrative of changing phase velocity while keeping the frequency-thickness product constant.

Figure 3:
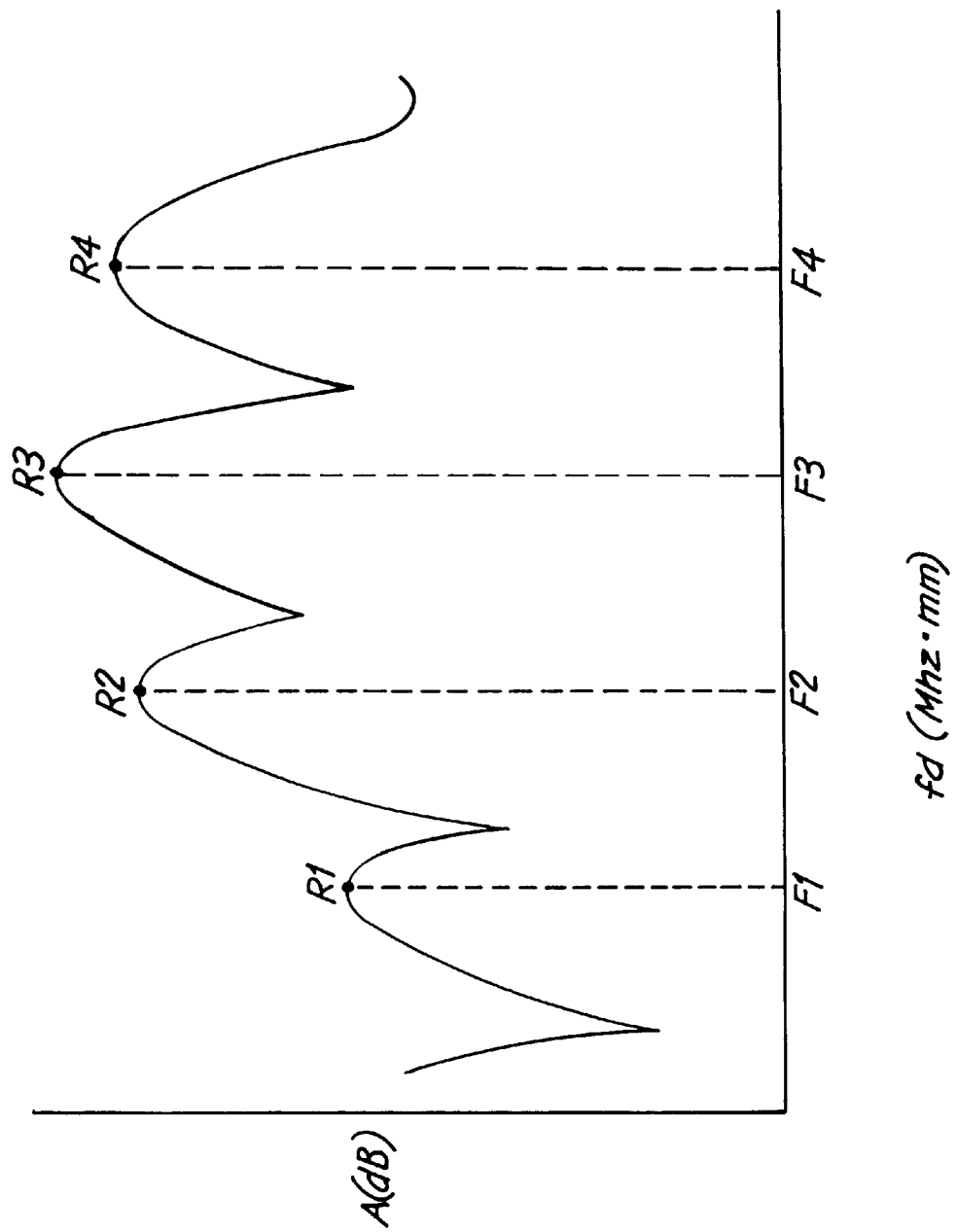
FIG. 3 is a graph of amplitude versus frequency of a received signal from a receiving transducer in a system configured in accordance with the present invention.

Referring now to FIG. 3, a graph illustrates amplitude versus frequency of a received signal from a receiving transducer in a system configured in accordance with the present invention. The transmitted signal has multiple frequency components and a constant phase velocity. The four peaks seen on the graph represent four resonance points R1–R4 where ultrasonic energy is transmitted with minimal loss. These peaks correspond to resonance points R1–R4 on the dispersion curve illustrated in FIG. 2. It is to be noted that the four points R1–R4 are found on four different mode lines Mode 2–Mode 5 of FIG. 2.

Referring now to FIGS. 2 and 3, the presence of surface contaminants may change the amplitude, frequency or phase velocity characteristics (or features) of points on the curve in FIG. 3, such as points R1–R4. The particular characteristic changed and the amount of change can be described as a type of "sensitivity" the resonance point has to a particular contaminant. It has been discovered that certain resonance points are highly sensitive to ice layers, but insensitive to water and/or glycol or other contaminants. These sensitivities could occur anywhere along the entire frequency spectrum from which features are extracted and used as input to a pattern recognition contaminant classifier. Alternatively, certain resonance points are highly sensitive to glycol, and insensitive to water and or ice or other contaminants. Other resonance points exhibit wave property changes in relation to the different mixtures of ice/water/glycol and other contaminants. By utilizing specific choices for transmission phase velocity and frequency, a small excitation zone with special penetration and sensitivity characteristics is possible. Every structure will have unique resonance points having these preferred characteristics. Applicants have discovered that when the appropriate resonance points are analyzed simultaneously, discrimination and classification of multiple surface contaminants is possible. Identifying the points can be accomplished using either theoretical modeling or empirical techniques. By mapping the response of a particular structure to different contaminants, a host controller system such as an expert system can be developed to provide a classification algorithm based on extracted features, feature ratios, and appropriate reference values. To this end, it is to be noted that it is impractical, if not impossible to excite exact resonance points because of variability in the detection system, the structure to be tested, and the contaminants themselves. In practicing the present invention, it is therefore necessary to excite relatively small excitation "zones". One such zone is illustrated in FIG. 2 as a shaded circle 150. Excitation of a small zone ensures excitation of the resonance point while providing meaningful classification data. Excitation of a frequency bandwidth of less than 0.5 Mhz·mm, and a phase velocity bandwidth of less than 0.5 mm/sec around the resonance points of interest is preferred to meet this objective.

For example, a structure can be tested using a plurality of resonance points having a common phase velocity. Each point would therefore have a unique frequency-thickness product. Line 152 of FIG. 2 illustrates how a common phase velocity can yield a number of resonance points. One or more of these points may satisfy system sensitivity requirements. Line 154 of FIG. 2 illustrates how a common frequency-thickness product can be utilized for a plurality of resonance points with different phase velocities. Different resonance points can be excited by sweeping along the lines, thereby eliminating a variable between measurements. Alternatively, the detection system of the present invention can be programmed to "jump" between resonance points by varying amplitude, phase velocity and frequency for each measurement as described hereinbefore. Whatever the sequence for excitation, each resonance point utilized will have propagation characteristics sensitive to a condition of interest. A contaminant may then be classified by transmitting several resonances and then carrying out appropriate feature extraction and pattern recognition techniques.

Guided waves can also be described in terms of particle movement having two vectorial components: a) particle wave motion in the direction of travel of the wave, otherwise known as polarized in-plane displacement (U), (i.e. parallel to the surface of the skin); or b) particle wave motion perpendicular to the direction of travel, otherwise known as polarized out-of-plane displacement (W) (i.e. normal to the surface of the skin). These displacement functions can be formulated as a function of the Eigen values or phase velocity values obtained in the generation of the dispersion curves. W displacement is sensitive to water detection because as the guided waves propagate along the skin, the presence of a W displacement causes leakage into the fluid, thereby severely reducing the amplitude of the wave. U displacement, on the other hand, is insensitive to water. Alternatively, both U and W displacements are sensitive to ice detection, because both result in absorption or energy leaking into the ice.

Transmission of guided waves having multiple vectorial components, (herein referred to as differently polarized or multipolarized waves) having a combination of U and W displacement on the exposed surface of the skin may be more effective and efficient in providing further classification of contaminants. For instance, a waveform may be utilized which has near equal U and W surface displacement. A particular contaminant may greatly attenuate this waveform, thereby providing additional classification information. In addition, the frequency and/or phase velocity of the waveform may be changed (as described hereinbefore) to extract further classification information.

Figure 4A:
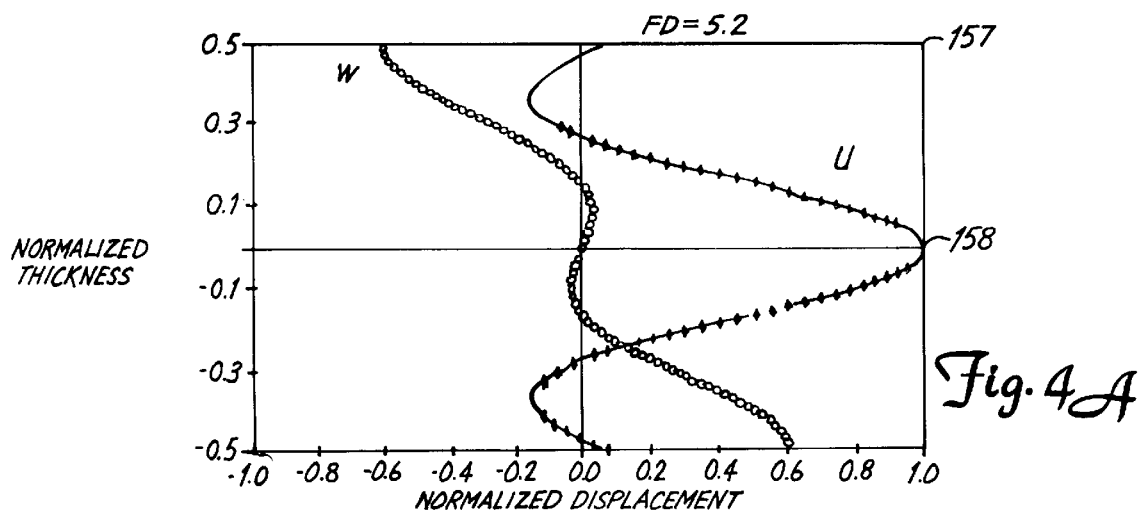
FIGS. 4a–4c are normalized amplitude distributions of U and W particle displacements plotted with respect to normalized skin thickness for four resonance points found on Mode 6 of the dispersion curve illustrated in FIG. 2.
Figure 4B:
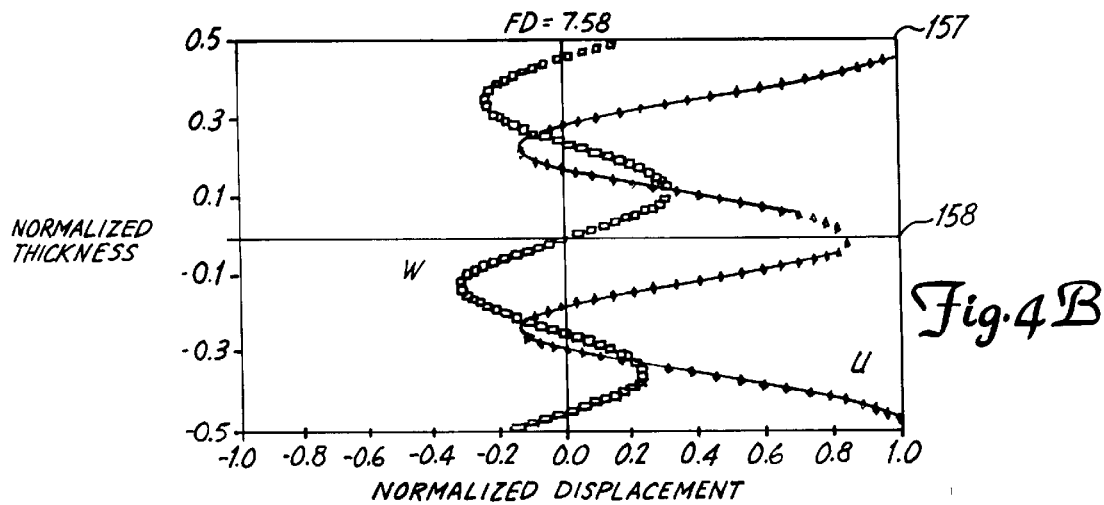
Figure 4C:
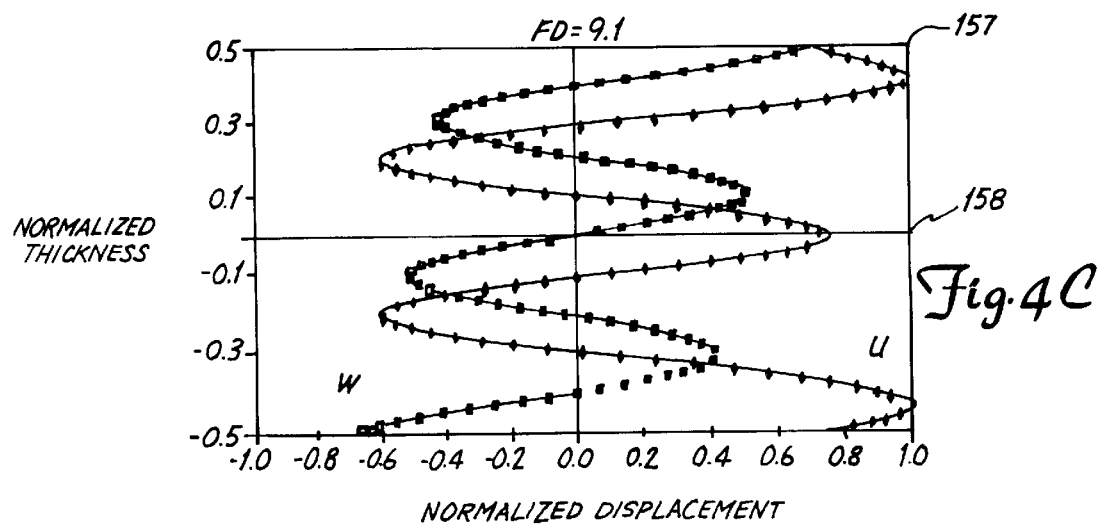

Referring now to FIGS. 4a–4c, wherein normalized amplitude distributions of U and W particle displacements are plotted with respect to normalized skin thickness for four resonance points found on Mode 6 of the dispersion curve illustrated in FIG. 2. It is to be noted that these points are only exemplary, and that the wave structure changes everywhere along the dispersion curve, and that changing any of a number of the conditions or parameters of the system results in a different wave structure. Top line 157 of each graph (i.e. a normalized thickness value of 0.5) represents the exposed surface of the skin. Displacement at this location therefore represents particle movement at the skin surface/contaminant interface. Also, although normalized displacement is plotted from −1.0 to 1.0, the absolute value of the displacement (rather than the actual value) is the meaningful number. It can be seen in FIGS. 4a–4d that U displacement is symmetrical about the center 158 of the skin while W displacement is antisymmetrical.

Referring now to FIG. 4a, wherein the normalized amplitude distributions of U and W particle displacements for a fd value of about 5.2 are illustrated. It can be seen that U displacement is near zero and W displacement is around 0.6 at the surface. This resonance point on the Mode 6 curve therefore has a predominant out-of-plane displacement component.

Referring now to FIG. 4b, wherein the normalized amplitude distributions of U and W particle displacements for a fd value of about 7.58 are illustrated. It can be seen that W displacement is near zero and U displacement is around 1.0 at the surface. This resonance point on the Mode 6 curve therefore has a predominant in-plane displacement component.

Referring now to FIG. 4c, wherein the normalized amplitude distributions of U and W particle displacements for a fd value of about 9.1 are illustrated. It can be seen that the W displacement and U displacement are around 0.7 at the surface. This resonance point on the Mode 6 curve therefore has nearly equal displacement vectorial components, or no predominant in-plane or out-of-plane displacement.

The resonance points illustrated in FIG. 4c may have a sensitivity which provides useful contaminant classification information for contaminants other than ice or water, or other contaminants unrecognizable with the points illustrated in FIGS. 4a and 4b. The usefulness of these points is, of course, dependent on a multiplicity of factors, such as skin material, airfoil configuration or structure, skin thickness, etc.

It is now apparent to those skilled in the art that contaminant classification is possible by first empirically or theoretically calculating the effect a variety of known contaminants might have on guided waves transmitted through a particular skin at specific resonance points or zones, and that the characteristics of the guided waves can be changed either by jumping between different modes on the dispersion curve or by staying on a single mode. The contaminant and wave conditions (frequency, mode, waveshape, amplitude, vectorial components, etc.) which yield the most sensitive or meaningful responses may be stored in a neural network. An expert system may then be utilized to ultrasonically stimulate the skin with a variety of guided waveforms, including differently polarized waveforms, and classify the actual contaminant in real time.

Figure 5A:
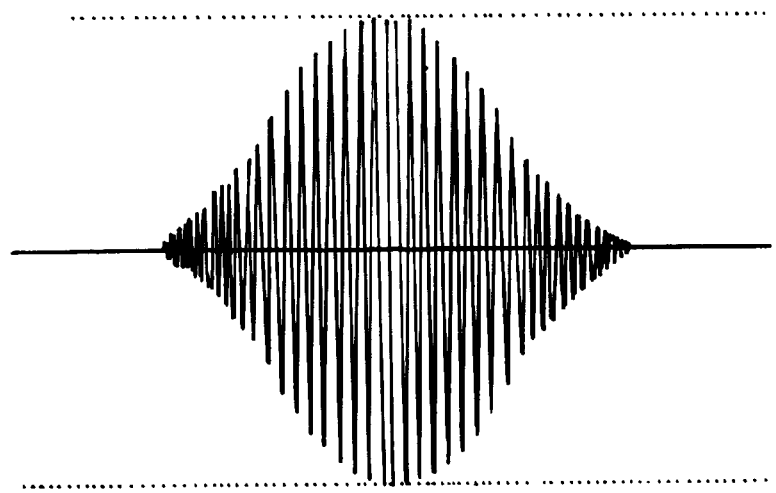
FIG. 5a is a graphical representation of a typical energy pulse for transmission through a skin in accordance with the present invention.

Referring now to FIG. 5a, a typical transmit signal provided by transmitter circuit 122 in accordance with the present invention is a shaped pulse as shown. Each pulse preferably has 4–50 cycles at a single frequency over a range of frequencies on the order of 0.2 Mhz–20 Mhz. It is to be noted that other waveforms may be utilized. For instance, the pulse may have a different shape, or the shape may be skewed to one side or the other or otherwise nonsymmetrical.

Figure 5B:
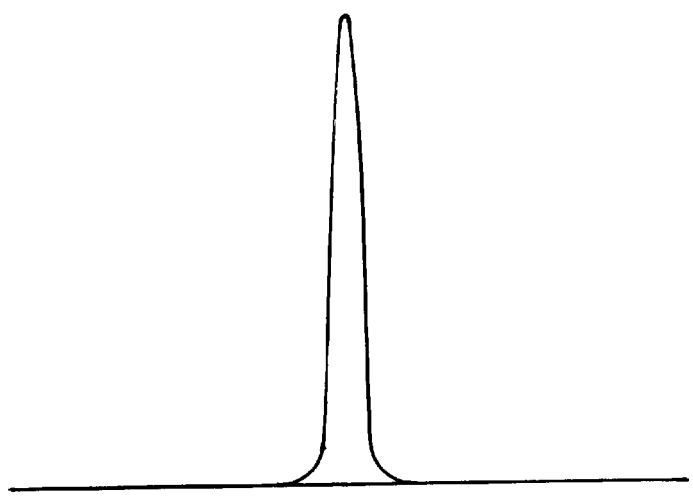
FIG. 5b is a graphical representation of a delta function energy pulse for transmission through a skin in accordance with the present invention.

Referring now to FIG. 5b, an alternative transmission pulse which may be utilized is a spike shaped pulse which approximates a delta function. This type of shock excitation pulse provides simultaneous transmission of a plurality, if not all of the critical dispersion curve resonances along a constant phase velocity line. The received signal would then be provided to the host controller for extrapolation of the transmission information using fast Fourier transforms (FFTs) or other digital signal processing methods. A received guided wave containing multiple resonances would be similar to the graph illustrated in FIG. 3. The entire frequency signature or specific features, such as peaks or valleys on the curve, could then be analyzed for classifying contaminants. Since a delta function pulse is a high energy pulse, a laser might be preferable for the transmission source.

Figure 6A:
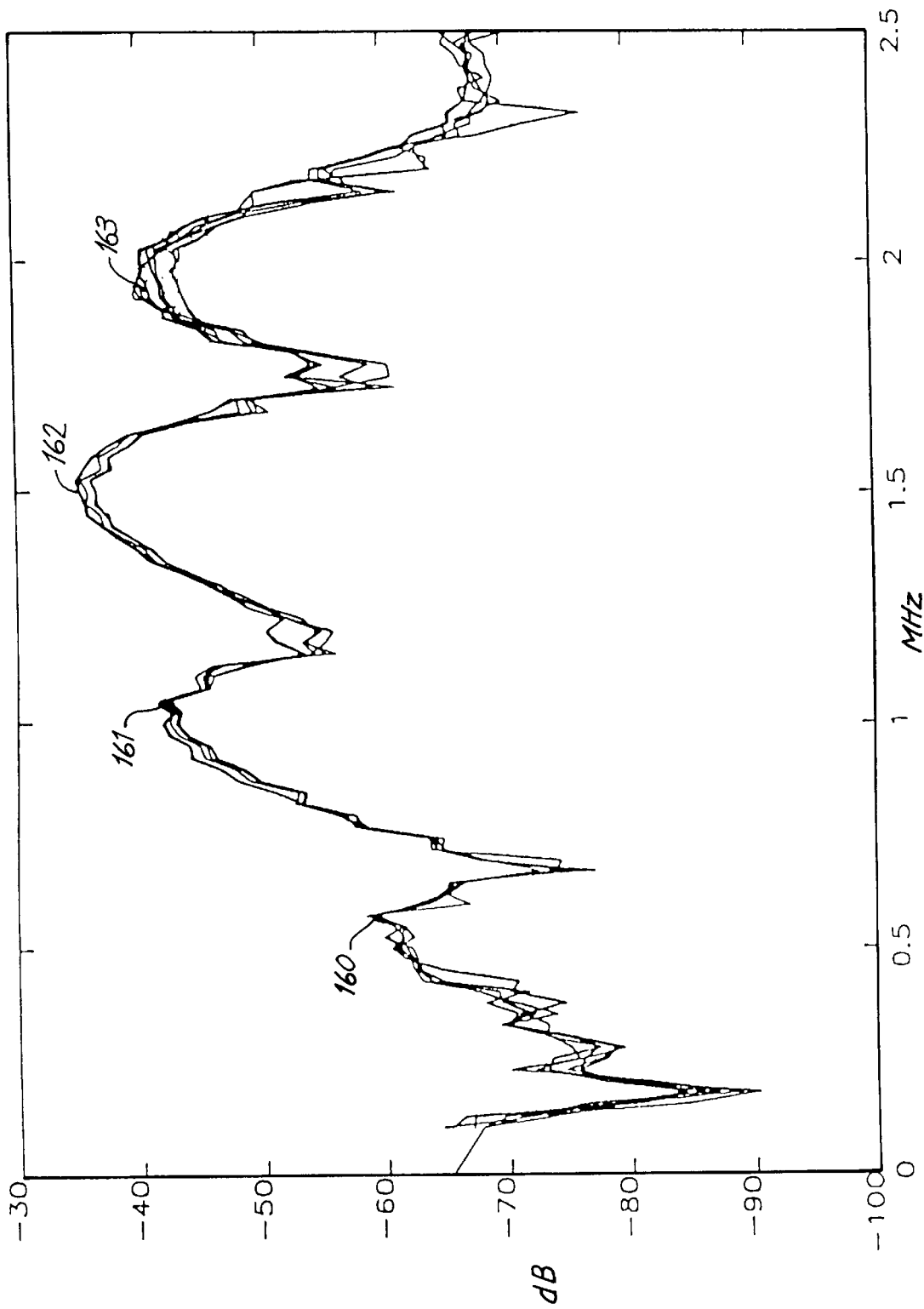
FIG. 6a is a graph of amplitude vs. frequency of a received signal from a guided wave transmitted through a 0.087 inch thick aluminum plate with no contaminants.

Referring now to FIG. 6a, a graph illustrates amplitude versus frequency of four received signals from a receiving transducer in a system configured similarly to that illustrated in FIG. 1. The skin through which the signal was transmitted was free of any contaminants. The incident angle of the transmit transducer was approximately 26.2°. The transmitted signal was a sweeping signal from 0–2.5 Mhz·mm. The peaks 160–163 in the curve correspond to theoretical points on the dispersion curve as frequency is swept across the curves at a common incident transmission angle (i.e. phase velocity). Sweeping a signal through a given frequency range at a specific incident angle is best illustrated in FIG. 2 as a horizontal line, such as line 152 or 156. Amplitude peaks 160–163 correspond to the intersection of the horizontal sweeping line with points on the theoretical dispersion curve for different resonance points. For instance, line 152 of FIG. 2 intersects points on the dispersion curve for Modes 2, 3, 4, 5, 6, and 7 in the fd range 0–12 Mhz·mm. The peaks 160–163 in FIG. 6a correspond to similar points of intersection for the 0–2.5 Mhz·mm range and an incident angle of 26°.

Figure 6B:
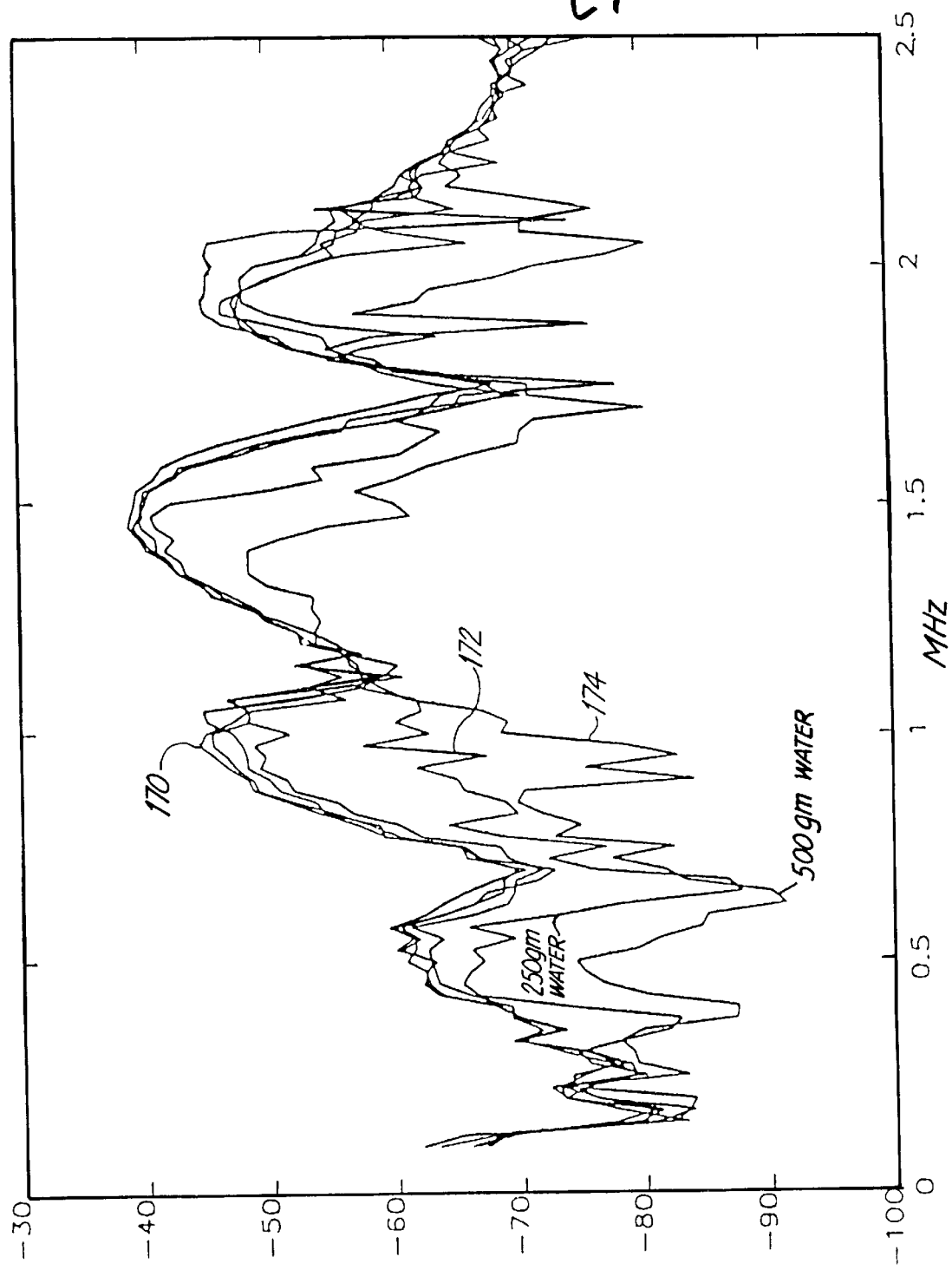
FIG. 6b is a graph of amplitude vs. frequency of a received signal from a guided wave transmitted through a 0.087 inch thick aluminum plate with water contaminant.

Referring now to FIG. 6b, wherein a graph similar to FIG. 6a is illustrated, but the skin is contaminated with various amounts of water. A line 170 represents a received signal from a skin having about 45 gm of deposited water. A line 172 represents a received signal from a skin having about 250 gm of deposited water. A line 174 represents a received signal from a skin having about 500 gm of deposited water. It can be seen from FIG. 6b that attenuation of the received signal is dependent upon the amount of water deposited on the skin.

Referring now to FIG. 6c, wherein a graph similar to FIG. 6a is illustrated, but the skin has been contaminated with various amounts of ice. A line 180 represents a received signal from a skin having about 35 gm of deposited ice. A line 182 represents a received signal from a skin having about 250 gm of deposited ice. A line 184 represents a received signal from a skin having about 500 gm of deposited ice. It can be seen from FIG. 6c that attenuation of the received signal is dependent upon the amount of ice deposited on the skin.

Figure 6D:
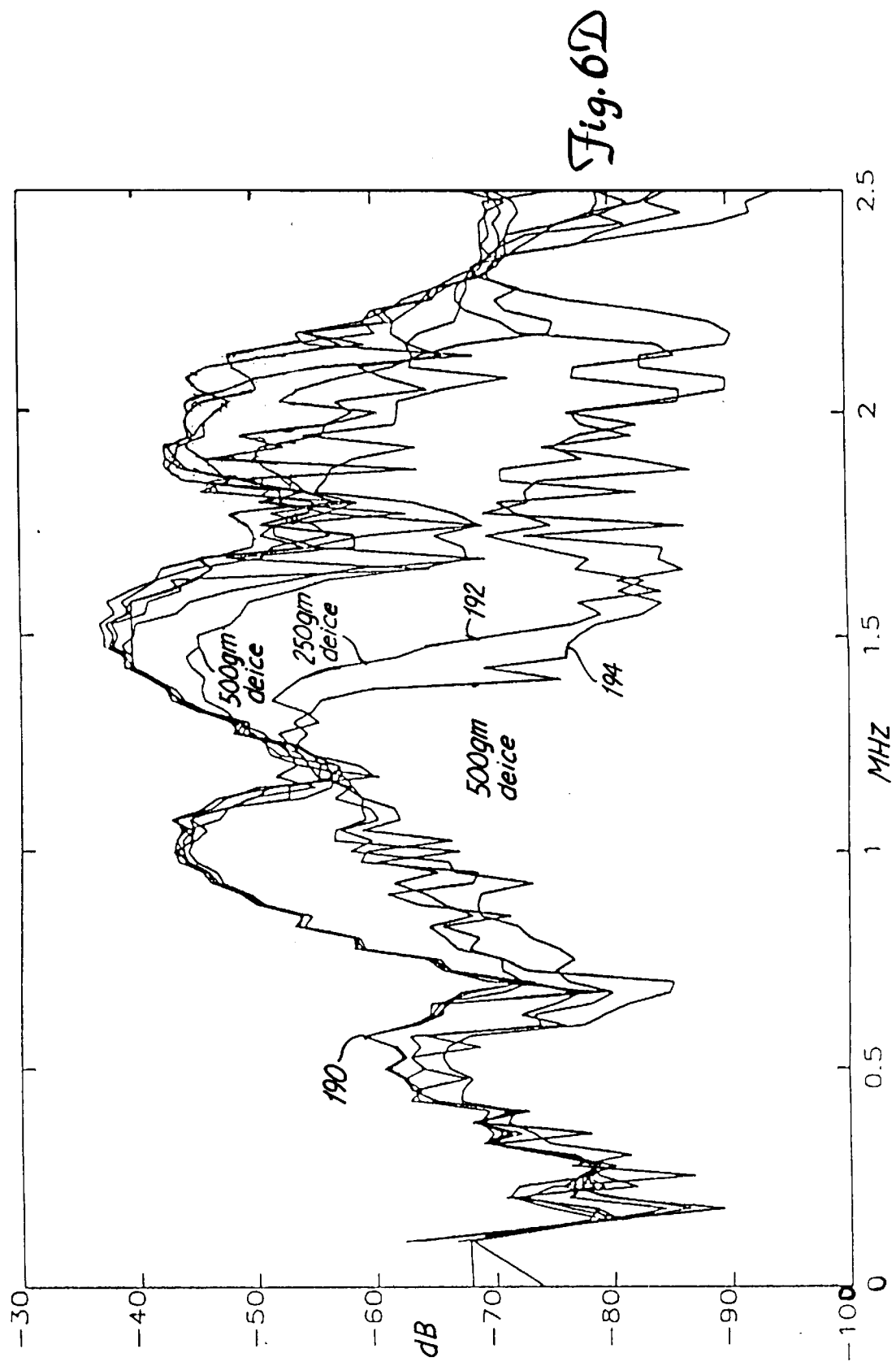
FIG. 6d is a graph of amplitude vs. frequency of a received signal from a guided wave transmitted through a 0.087 inch thick aluminum plate with glycol contaminant.

Referring now to FIG. 6d, wherein a graph similar to FIG. 6a is illustrated, but the skin has been contaminated with various amounts of glycol. A line 190 represents a received signal from a skin having about 35 gm of deposited glycol. A line 192 represents a received signal from a skin having about 250 gm of deposited glycol. A line 194 represents a received signal from a skin having about 500 gm of deposited glycol. It can be seen from FIG. 6d that attenuation of the received signal is dependent upon the amount of glycol deposited on the skin.

Figure 7:
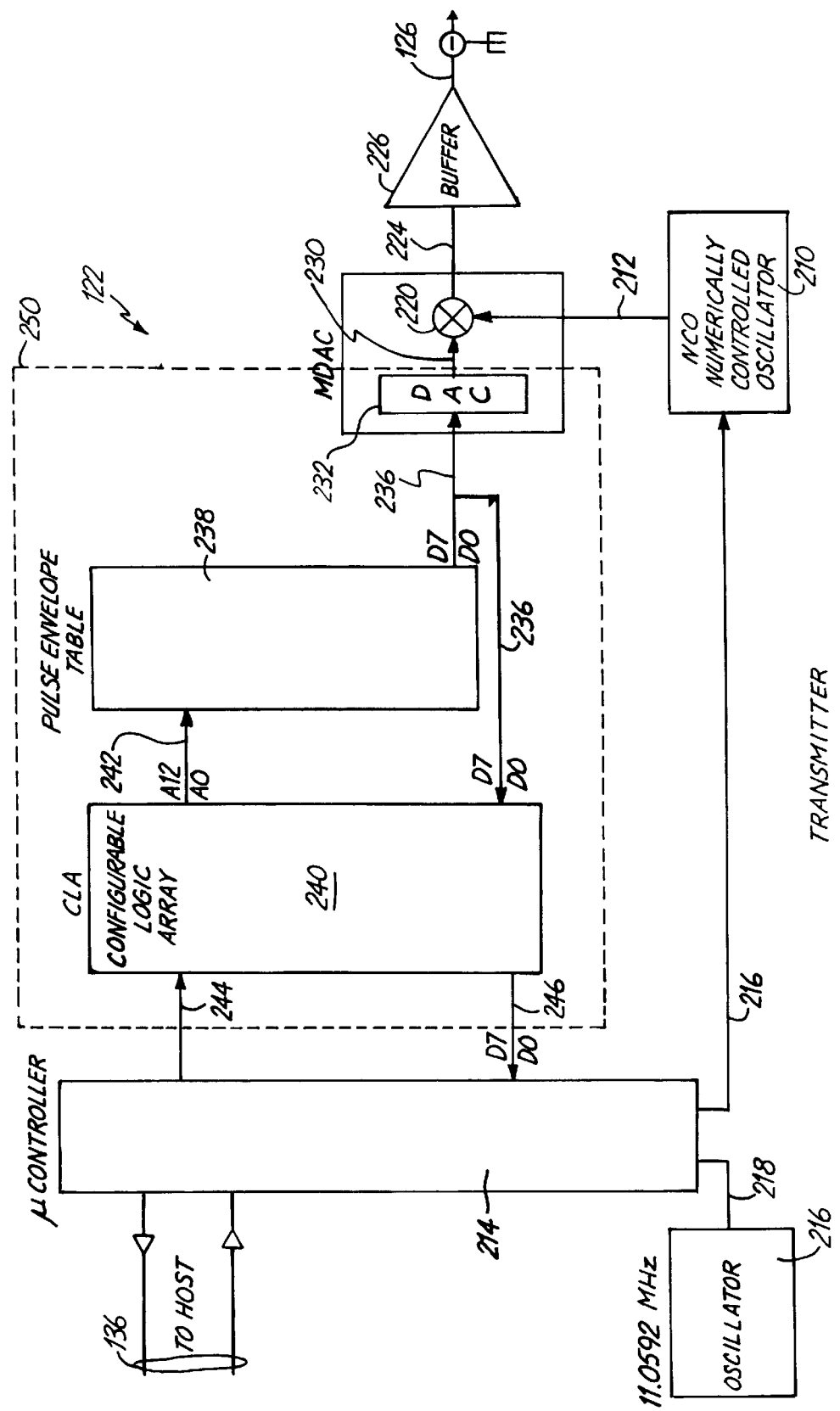
FIG. 7 is a schematic block diagram of a transmitter circuit for a contaminant detection system in accordance with the present invention.

Referring now to FIG. 7, a transmitter 122 for providing a pulse of electrical energy to transducer 110 includes a numerically controlled oscillator (NCO) 210 utilized to provide a sinusoidal waveform at a specified frequency on a line 212. The frequency of the NCO 210 may be varied from approximately 100 KHz to 10 Mhz. The NCO 210 is controlled by a microprocessor (CPU) 214 via a line 216. CPU 214 is controlled by the host processor via a line 136. An oscillator 216 provides a clock signal on a line 218 to CPU 214. The transmit carrier frequency waveform on line 212 is provided to a modulator 220 which modulates the signal into pulses of energy envelopes provided on a line 224 to a buffer 226 which provides a buffered pulse energy envelope signal on a line 228 to the transmit transducer 110. Modulator 220 is controlled by a modulation control signal provided on a line 230 from a D/A converter 232. D/A converter 232 is provided input on a data line 236 from a pulse envelope memory unit 238. The pulse envelope table memory 238 is controlled by a configurable logic array (CLA) 240 via data line 242. The configurable logic array 240 is controlled by the CPU 214 via a data line 244. The configurable logic array 240 also receives the output envelope data on line 236 to provide feedback data on a line 246 to the CPU 214. The CLA 240, pulse envelope memory unit 238, and D/A converter 232 make up an envelope generator to modulate the sinusoidal waveform provided on line 212 from the NCO 210 and provide a pulse of energy at a specific frequency on line 224. The envelope generator 250 provides control over the pulse length, pulse shape, and pulse amplitude of the transmit waveform. The pulse length can be controlled from 30 nS and up. The pulse amplitude can be set to one of 255 non zero power level output settings. Providing control over pulse amplitude as a function of time allows the creation of shaped pulses of energy at a given carrier frequency. This control over pulse length and pulse shape provides for control over the spectral content of the transmit waveform.

Figure 8:
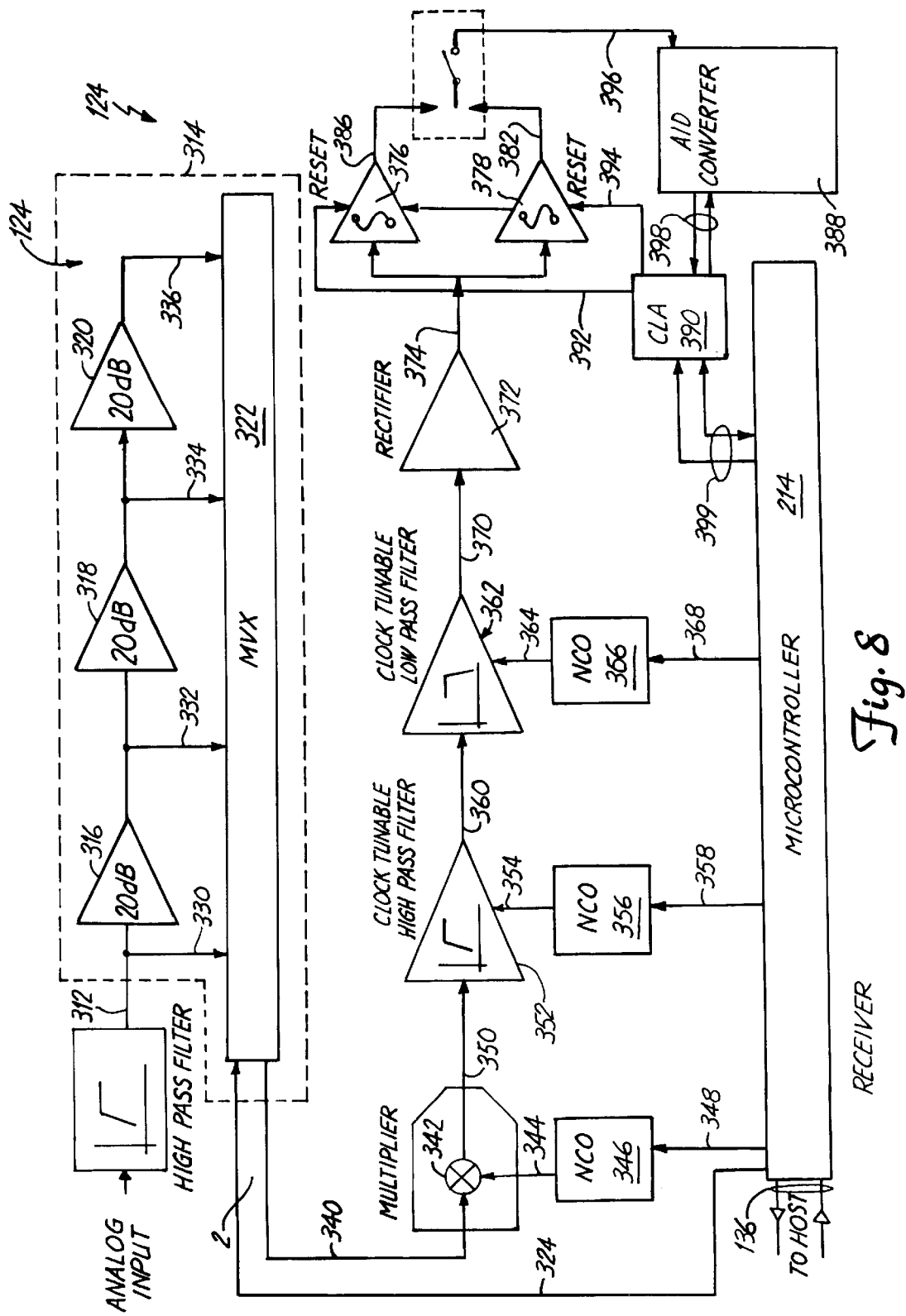
FIG. 8 is a schematic block diagram of a receiver circuit for a contaminant detection system in accordance with the present invention.

Referring now to FIGS. 1 and 8, the electrical signal output from the receive transducer 112 is provided on a line 132 to a high pass filter 310. The filtered signal is provided on a line 312 to a selectable gain stage 314 comprised of a plurality of amplifiers 316, 318, 320 and a multiplexer 322. A plurality of "taps" on lines 330, 332, 334, 336 are provided to the multiplexer 322, which is controlled by CPU via a line 324. The amplified signal from multiplexer 322 is provided on a line 340 to an analog mixer 342. Analog mixer 342 combines the received signal on line 340 with a sinusoidal waveform provided on a line 344, from a NCO 346, which is controlled by CPU 214 via a line 348. A resultant intermediate frequency signal is provided from the mixer 342 on a line 350 to a clock tunable high pass filter 352 which is tuned by a clock signal provided on a line 354 from a NCO 356, which is controlled by CPU 214 via a line 358. The output of the high pass filter 352 is provided on a line 360 to a clock tunable low pass filter 362 which is tuned via a clock pulse provided on a line 364 from a NCO 366 which is controlled by CPU 214 via a line 368. Filters 352 and 362 comprise a band pass filter. The resultant filtered signal is provided on a line 370 to a rectifier 372. A rectified signal is provided on a line 374 to a pair of identical integrators 376, 378 which run with a 50% overlap. The output of integrators 376, 378 are provided on lines 380, 382 respectively to a sampler 384, which alternately switches the two signals and provides the output on a line 386 to an A/D converter 388. Integrators 376, 378 and sampler 384 are controlled by a CLA 390 via lines 392, 394, 396, respectively. The digital output samples of A/D converter 388 is sent to CLA 390 via line 398. The data is collected and stored by CPU 214 via a line 399 until the end of the "listen interval". At the end of the "listen interval", the CPU 214 returns the data results to the host computer via line 136.

NCO 346 is utilized to provide numerically controlled sine waves to control the local oscillator frequency used by the mixer 342. Controlling the transmit frequency via NCO 210 and the local oscillator frequency via NCO 346 provides control over the intermediate frequency.

NCO 356 and NCO 366 utilized in conjunction with filters 352 and 362 to provide low pass and high pass filter functions. These two filters are utilized to provide a band pass filter where the band width and the center frequency can be easily controlled. As the spectral content of the transmit pulse changes, the receiver can be configured to maximize the signal to noise ratio by appropriately adjusting the band width of the receiver.

The integration time is also easily changed. The integration time is typically chosen to be equal to the pulse length used for the transmit pulse. The intent is to capture as much energy as possible from a given pulse during one integration cycle. The ability to change this parameter to a different value provides a means of adapting to situations where pulse elongation occurs.

The "listen interval" is another variable easily altered. This value determines how many integrator samples are collected prior to sending results back to the host computer 134. This parameter, along with the transmit pulse length, will determine the pulse repetition rate of the system.

CPU 214 communicates to the host computer 134, preferably through an RS-232 serial communications port operating at 19.2 kbps. The host computer sets the following parameters through commands issued through the communications port: transmit oscillator frequency; transmit envelope; mixer oscillator frequency; low pass filter corner frequency; listen interval; transmit pulse length; receiver gain; high pass filter corner frequency; and integration time. Once the above parameters have been specified, a pulse can be generated and the received signal data points collected. The data is then returned to the host processor 134 for processing. The host can then determine both the arrival time and the peak of the signal measured during the listen interval. The gain of the CDS 100 can then be changed, if necessary and the measurement retaken.

Measurements can easily be performed at single frequencies with narrow bandwidth. Many single frequency measurements can be used to create a frequency spectrum. The start frequency, stop frequency and frequency step are all under the control of the host controller 134.

Figure 9:
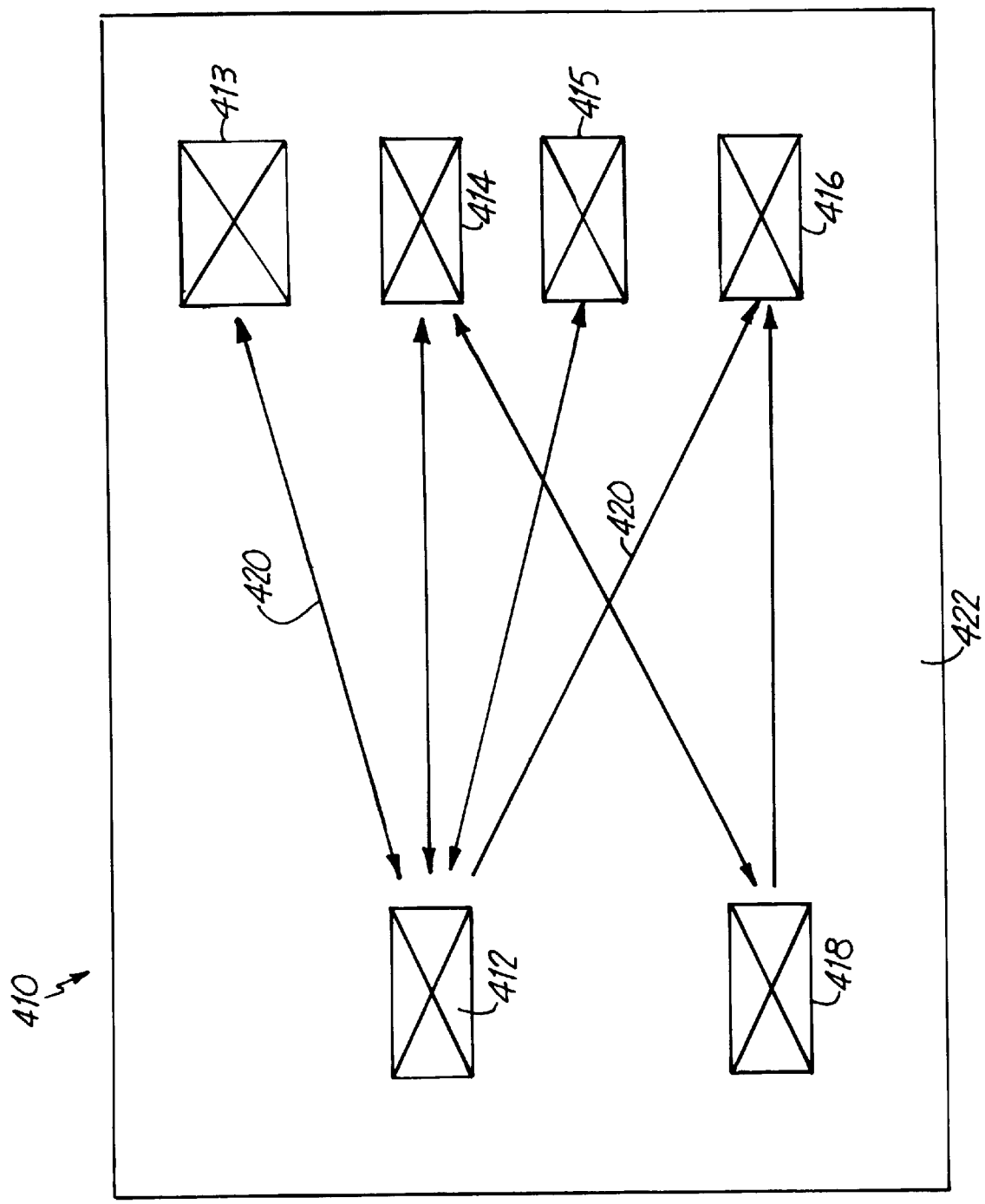
FIG. 9 is a schematic block diagram of a configuration for positioning transducer elements in accordance with the present invention.

Referring now to FIG. 9, a contaminant detection system 410 in accordance with the present invention comprises six transducer elements 412, 413, 414, 415, 416, 418. Guided waves represented by arrows 420 can be sent between elements to thereby cover an area of interest on airfoil 422. This configuration therefore can "cover" an airfoil area larger than a system utilizing only two transducers. Of course, any of a number of different configurations and combinations may be utilized. For instance, a single transducer 412 may be used to transmit to a plurality of transducers 413–415 as the transmitted wave fans out.

Figure 10:
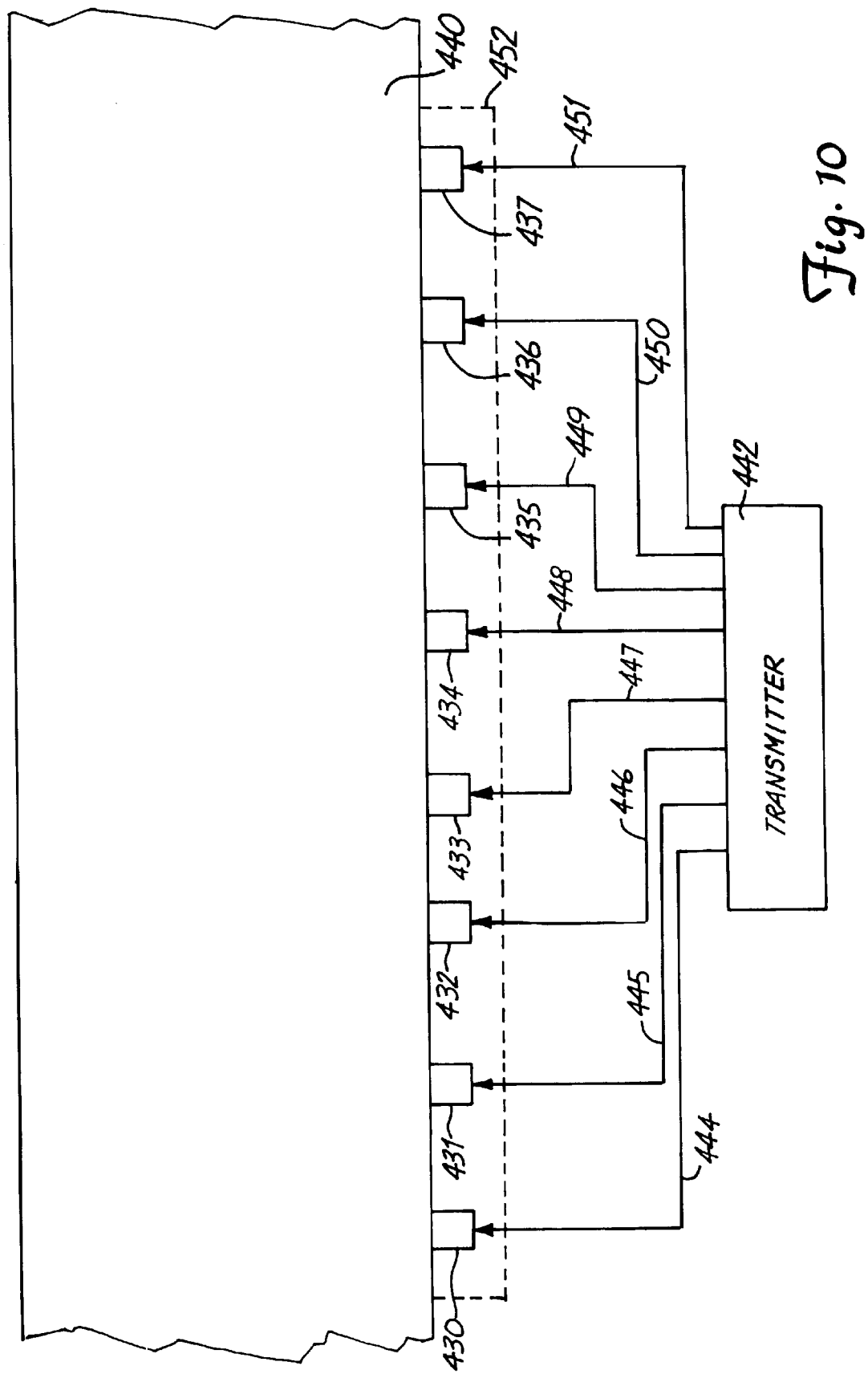
FIG. 10 is a schematic block diagram of an alternative embodiment of a transmitting portion of a contaminant detection system in accordance with the present invention.

Referring now to FIG. 10, an alternative embodiment of the present invention includes a plurality of transducers 430–437 which are disposed on a skin 440 in a comb type configuration. A transmitter 442 drives the transducers through lines 444–451. This approach can produce phase velocity and frequency values of choice in selecting the best resonance points of interest on the dispersion curve. The transducers may be contained or potted within a common housing 452 for convenience.

Figure 11:
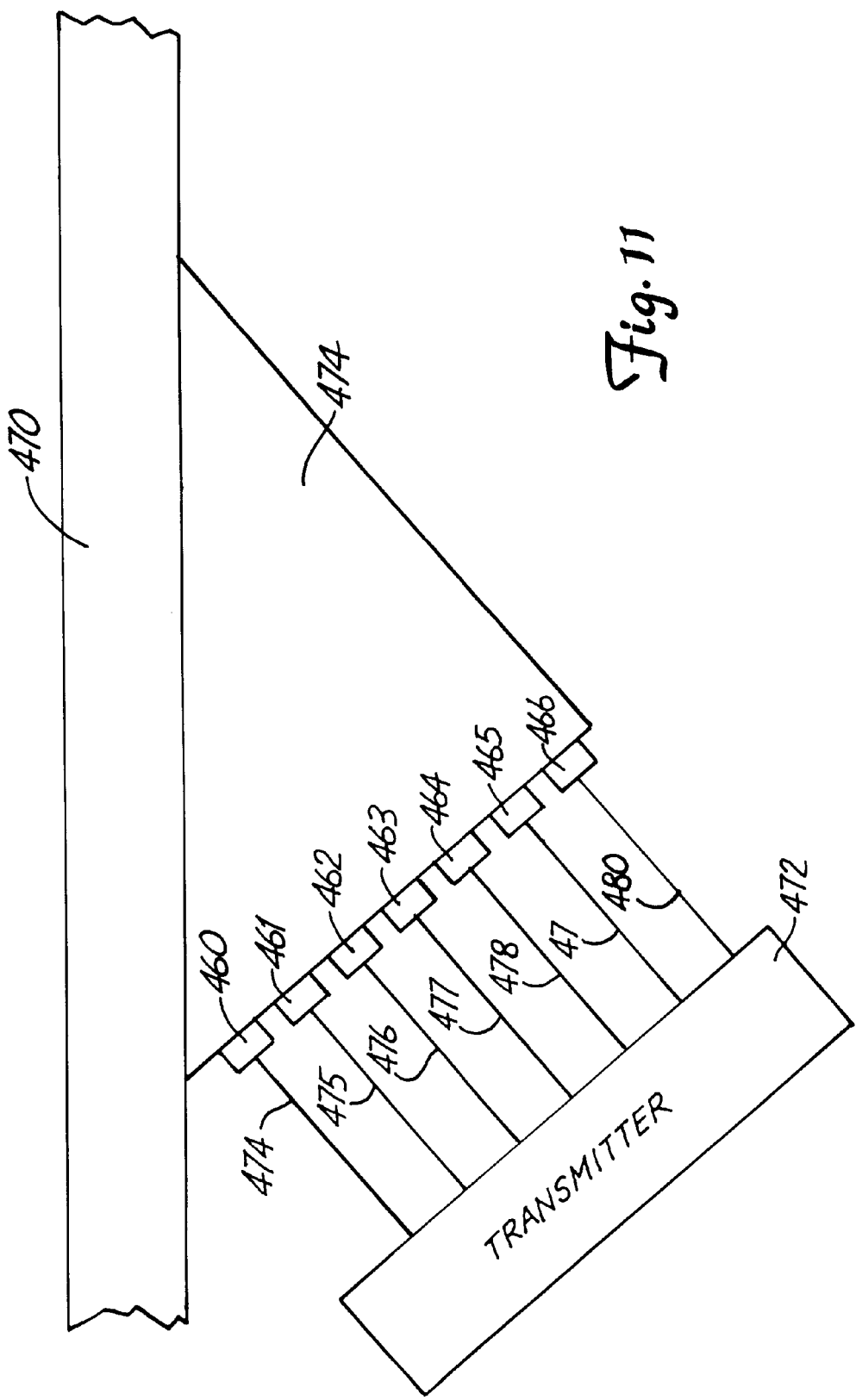
FIG. 11 is a schematic block diagram of an alternative embodiment of a transmitting portion of a contaminant detection system in accordance with the present invention.

Referring now to FIG. 11, an alternative embodiment in accordance with the present invention includes a plurality of transducers 460–466 which are disposed on a coupler at a predetermined angle to a skin 470 in an array type configuration. A transmitter 472 drives the transducers through lines 474–480. Controlling the transducers with a time delay profile effectively changes the phase velocity via an effective incident angle change. An alternative embodiment could consist of a non-contact ultrasonic sender and a capacitive type receiving transducer particularly if distance between sender and receiver is small. Other non-contact excitation or reception might be possible with an electromagnetic transducer (EMAT) or even a laser pulse transducer to produce guided waves.

A pulse echo type system could also be used opposed to thru transmission with a sender and a receiver. One transducer could be used both as sender and receiver whereby an edge reflection is possible depending on the structure being examined or even a wave guide consisting of a thin metal strip or tape that detects leakage of ultrasonic energy onto it and redirects it into a specific direction.

Transmitters 442 and 472 in FIGS. 10 and 11 can vary the selection of which transducer(s) is/are pulsed at a particular time. By varying the type of pulse, the transducer(s) selected and the sequence of transducer pulsing, and other parameters, different resonance points on the dispersion curve can be obtained. For example, different effective incident angles can be obtained by sequentially pulsing each transducer and varying the time delay between successive pulses. Likewise every other transducer may be pulsed sequentially, simultaneously or some other sequence. It is also to be noted that although eight and seven transducers are shown, respectively, a different number may be utilized.

It is also to be noted that FIGS. 10 and 11 illustrate a transmitter transducer, and that the receiving portion could also have a transducer array similar to the transmitter array, or simply be a single element.

Figure 12:
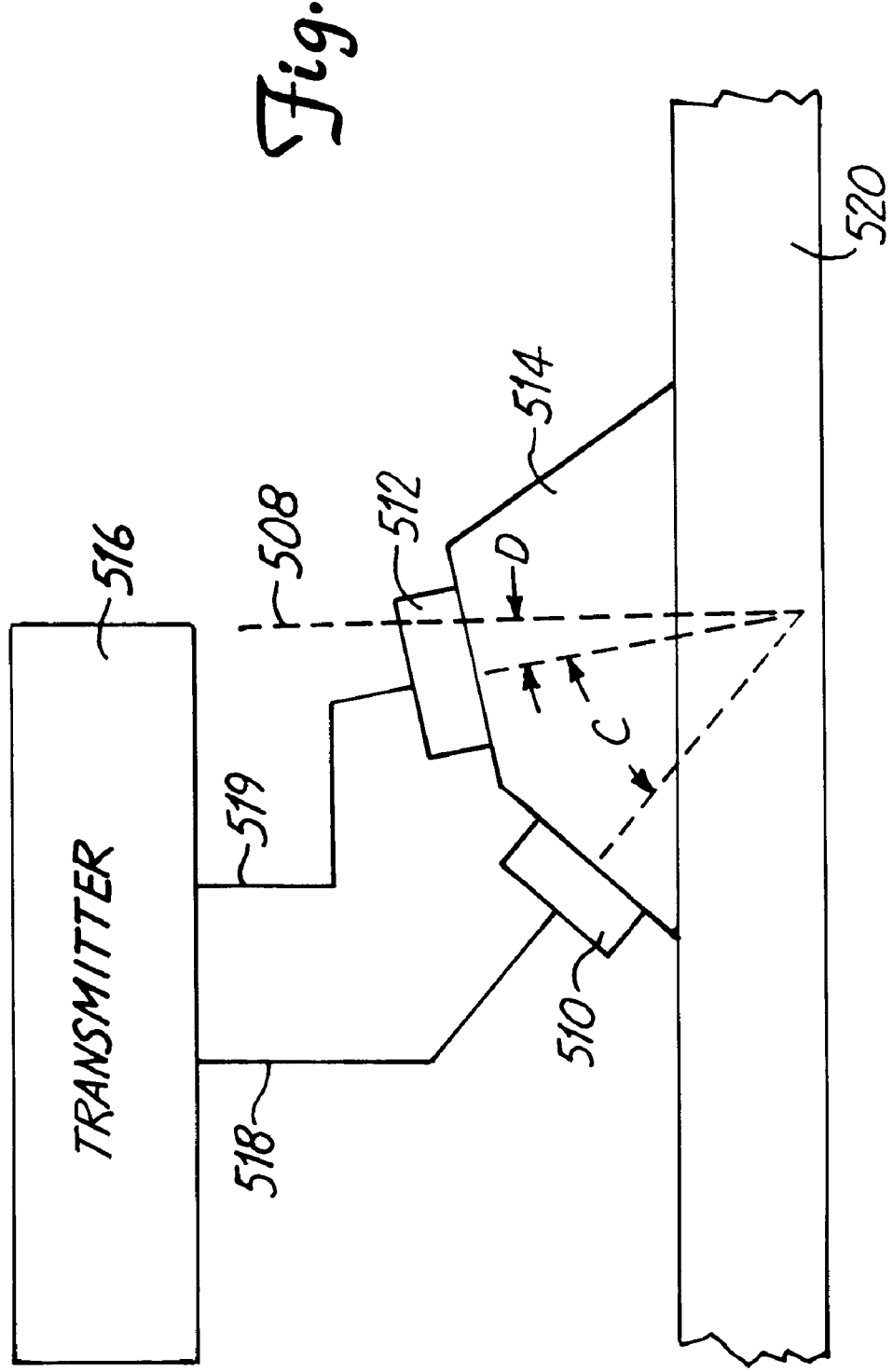
FIG. 12 is a schematic block diagram of an alternative embodiment of a transmitting portion of a contaminant detection system in accordance with the present invention.

Referring now to FIG. 12, an alternative embodiment in accordance with the present invention includes a pair of transducers 510, 512 disposed on a coupler 514 at different predetermined angles C,D to a line 508 which is normal to a skin 520. A transmitter 516 drives the transducers through lines 518, 519. It has been found that for a 0.125 inch plate, the most efficient contaminant data collection sequence is obtained if Angle C is on the order of 26° and Angle D is on the order of 38°. Of course, more than two transducers disposed at more than two different angles may be utilized.

Figure 13A:
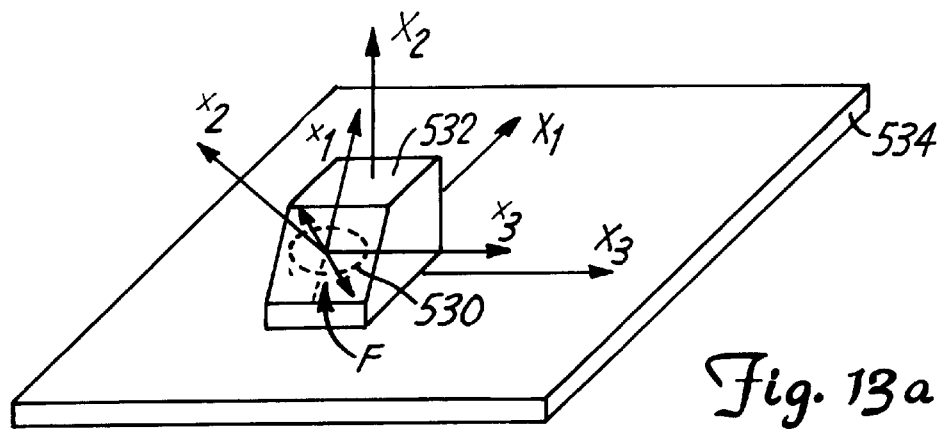
FIG. 13a is an isometric view of an alternative embodiment of a transducer and coupler for a contaminant detection system in accordance with the present invention.
Figure 13B:
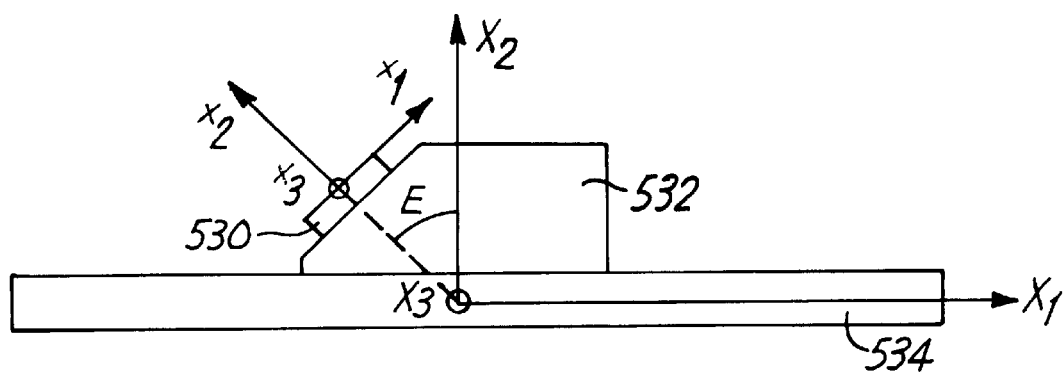

Referring now to FIGS. 13a and 13b, an alternative embodiment in accordance with the present invention includes a shear wave transducer 530 disposed on a coupler 532 at a predetermined angle E to a skin 534 at a particular orientation angle F. In addition to guided wave modes which exist in flat layers, there also exist time harmonic wave motions known as shear horizontal (SH) modes. The term horizontal shear means that the particle vibrations (displacements and velocities) caused by any of the SH modes is in a plane which is parallel to the surfaces of the layer. The orientation (angle F) of the transducer 530 on the surface of the coupler 530 determines how much of the incident energy goes into generating guided waves and how much goes into generating shear horizontal (SH) waves. Since SH wave modes are a synthesis of pure in-plane shear waves, the tractions applied to the surface of the layer must also have an out-of-plane shear component. This is achieved by providing a viscous couplant (not shown), such as silicone or an adhesive between the coupler 530 and skin 532. If transducer 530 is a shear wave contact transducer, particle vibration in the coupler will lie in the $x_1$–$x_3$ plane. The relative amount of $x_1$ and $x_3$ displacements will be a function of angles E and F. If angle F is 0, the polarization direction of the transducer coincides with the $x_1$ axis and all of the incident energy goes into guided wave modes. As angle F is increased, energy partition between guided wave and SH modes is equal for an angle F of 45°. For angle F≧72°, over 90% of the incident energy goes into the SH modes. To maximize the amount of energy which is put into the SH modes, the angle F should be as close as possible to 90°. It can be seen that angle F does not equal 90°, both SH and guided modes can be generated simultaneously.

Figure 14:
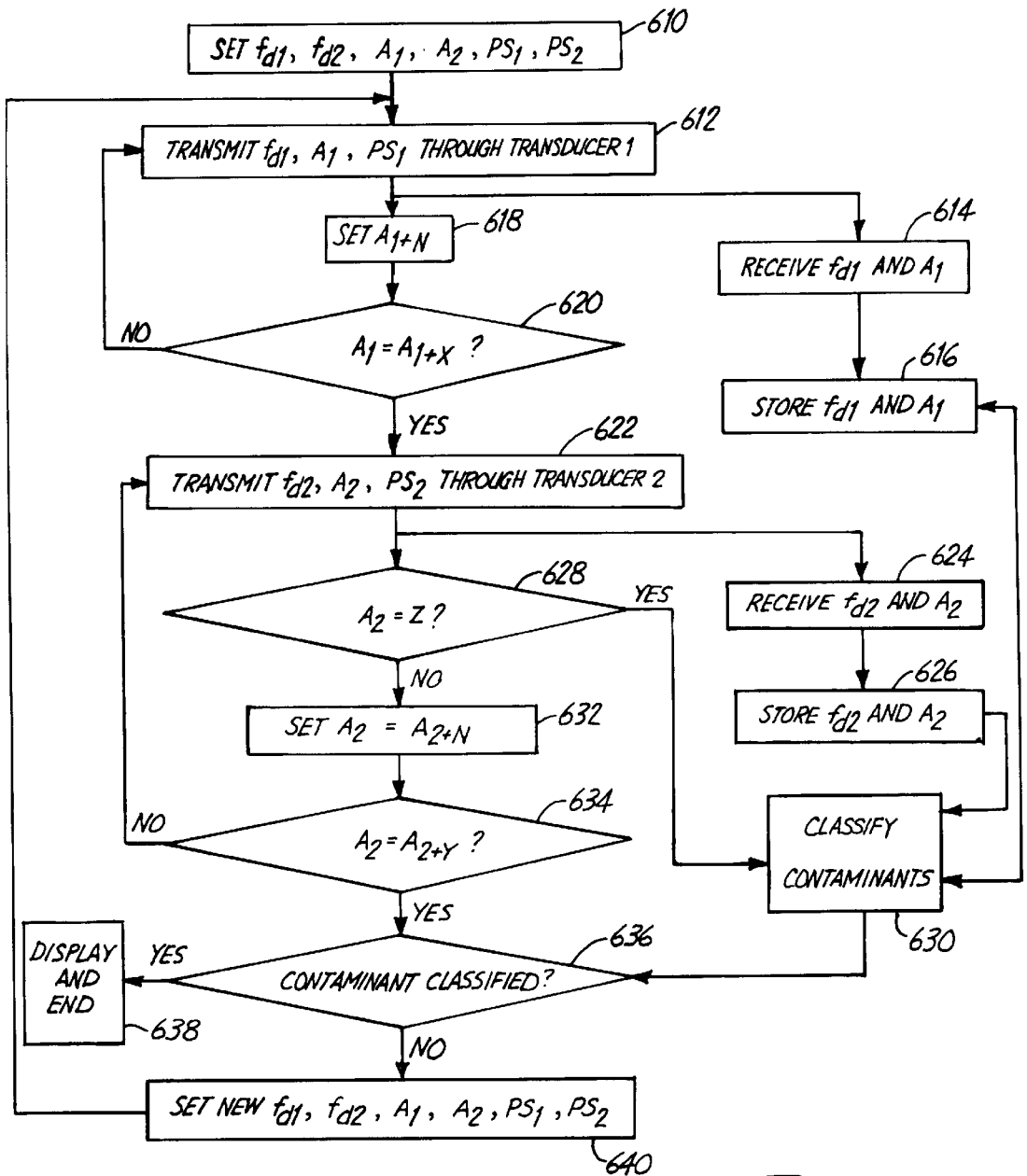
FIG. 14 is a flow chart for collecting contaminant classification data for a contaminant detection system in accordance with the present invention.

Referring now to FIG. 14, a flow chart for collecting contaminant classification data in accordance with a contaminant detection system similar to FIG. 1, but having a pair of transmit transducers similar to those illustrated in FIG. 12 includes a step 610, wherein the host controller sets a first pulse frequency $f_{d1}$, a second pulse frequency $f_{d2}$, a first pulse amplitude $A_1$, a second pulse amplitude $A_2$, a first pulse shape $PS_1$, and a second pulse shape $PS_2$. In a step 612, the host controller commands a first transmit transducer to transmit a guided wave having the $f_{d1}$, $A_1$, $PA_1$ characteristics through the skin. In steps 614, 616 the transmitted pulse is received by the receiving transducer, digitized and stored by the host controller. A new amplitude is set by the host controller in a step 618 to $A_{1+N}$. The incremented amplitude is checked to verify it has not exceeded a predetermined value $A_{1+X}$ in a step 620. If the $A_{1+N}$ does not equal $A_{1+X}$ then the incremented frequency is transmitted in step 612. If $A_{1+N}$ equals $A_{1+X}$ then the first transmit cycle has transmitted a first shaped pulse at a first phase velocity (determined by the incident angle of the first transmit transducer). The host controller then commands, in a step 622, a second transmit transducer to transmit a guided wave having the $f_{d2}$, $A_2$, $PA_2$ characteristics through the skin. In steps 624, 626 the transmitted pulse is received by the receiving transducer, digitized and stored by the host controller. The amplitude is checked to verify it has not exceeded a predetermined value Z in a step 628. If the amplitude has reached Z, the host controller utilizes the data collected and stored in steps 614, 616, 624 and 626 to classify the contaminant using fuzzy logic, neural networks, fast fourier transforms, or other digital processing tool known to those skilled in the art. If the amplitude does not equal Z, then a new amplitude is set by the host controller in a step 632 to $A_{2+N}$. The incremented amplitude is checked to verify it has not exceeded a predetermined value $A_{2+Y}$ in a step 634. If the $A_{2+N}$ does not equal $A_{2+Y}$ then the incremented frequency is transmitted in step 622. If $A_{2+N}$ equals $A_{2+Y}$ then the second transmit cycle has swept through a second frequency range at a second phase velocity (determined by the incident angle of the second transmit transducer). Determination is then made in a step 636 of whether the contaminant, if any, has been classified. If the contaminant has been classified, then the results are displayed and the sequence is ended in a step 638. If the contaminant has not been classified, a new first pulse frequency $f_{d1}$, second pulse frequency $f_{d2}$, first pulse amplitude $A_1$, second pulse amplitude $A_2$, first pulse shape $PS_1$, and second pulse shape $PS_2$ are set by the host controller in a step 640 and another round of pulse transmission and contaminant detection and classification begins at step 612.

It is to be noted that two different transmission resonance points can be achieved by transmitting pulses at a first frequency at a first incident angle and then at a second frequency at a second incident angle, thereby picking out different resonance points on the dispersion curve for the skin.

Referring now to FIGS. 15A, 15B, an alternative embodiment in accordance with the present invention includes a contaminant detection sheet 710, 712 disposed on top of an airfoil 720. An ultrasonic transmitting probe 716 transmits guided waves through coupler 714, and sheets 710, 712 and are received by a receiving probe 722 through a coupler 724. Probes 716, 722 are controlled via lines 718, 726, respectively. Utilization of contaminant detection sheets 710, 712 which are disposed on top of the airfoil eliminates many of the problems associated with transmitting directly through the airfoil itself because airfoils have inconsistent thickness, cracks, chemically milled cutout areas, and other anomalies, and structural members (such as braces, rivets, etc.) provided therein. All of these airfoil characteristics have a disruptive effect on the transmission of guided waves. Sheets 710, 712 are uniform in thickness, etc. and thereby provide predictable transmission results that are universal from aircraft to aircraft. In addition, these sheets may be easily replaced if they become damaged.

Referring now to FIGS. 16A, 16B, an alternative embodiment in accordance with the present invention includes contaminant detection sheets 730, 732 which are disposed on top of an airfoil 734. An ultrasonic probe 736, 737 transmits and receives guided waves through a coupler 738 and is controlled via a line 740. In this manner, only one probe is necessary to do contaminant classification. Probe 736 may be disposed at or near the focal point of the ellipse for more efficient utilization of the wave energy. Sheets 730, 732 are similar to those described in FIGS. 15A, 15B but have rounded, elliptical, or other shaped ends 739, 738, 740. The shape of the end will, of course, depend on appropriate signal analysis. Elliptical ends are preferred because all of the path lengths from a probe through the material and back to the probe are equal. This means that a pulse of energy placed into an elliptically shaped aluminum plate will have all its energy arrive back at the same time.

Sheets 710, 712, 730, 732 may be either bonded to the top of the airfoil or attached utilizing an attachment means, such as rivets, screws, nuts and bolts, etc. It is to be noted, however, that the sheets should be acoustically isolated from the airfoil surface for best results. It is therefore recommended to provide an acoustic mismatch between the two surfaces to prevent the sheets from appearing acoustically as a much thicker sheet. Various adhesives, foams, or pads may be utilized to acoustically isolate these sheets from the airfoil.

Figure 17A:
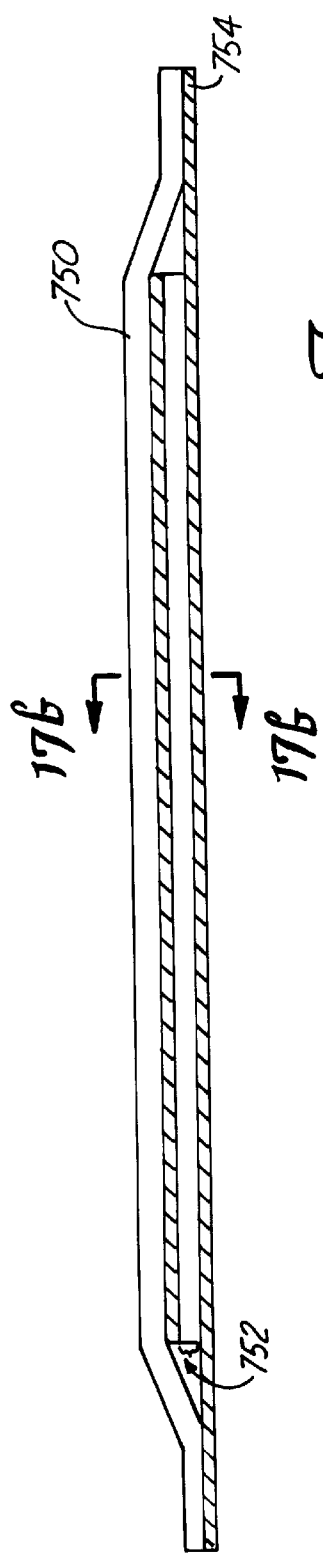
FIG. 17a is a side view of an alternative embodiment of a contaminant detection system in accordance with the present invention.
Figure 17B:
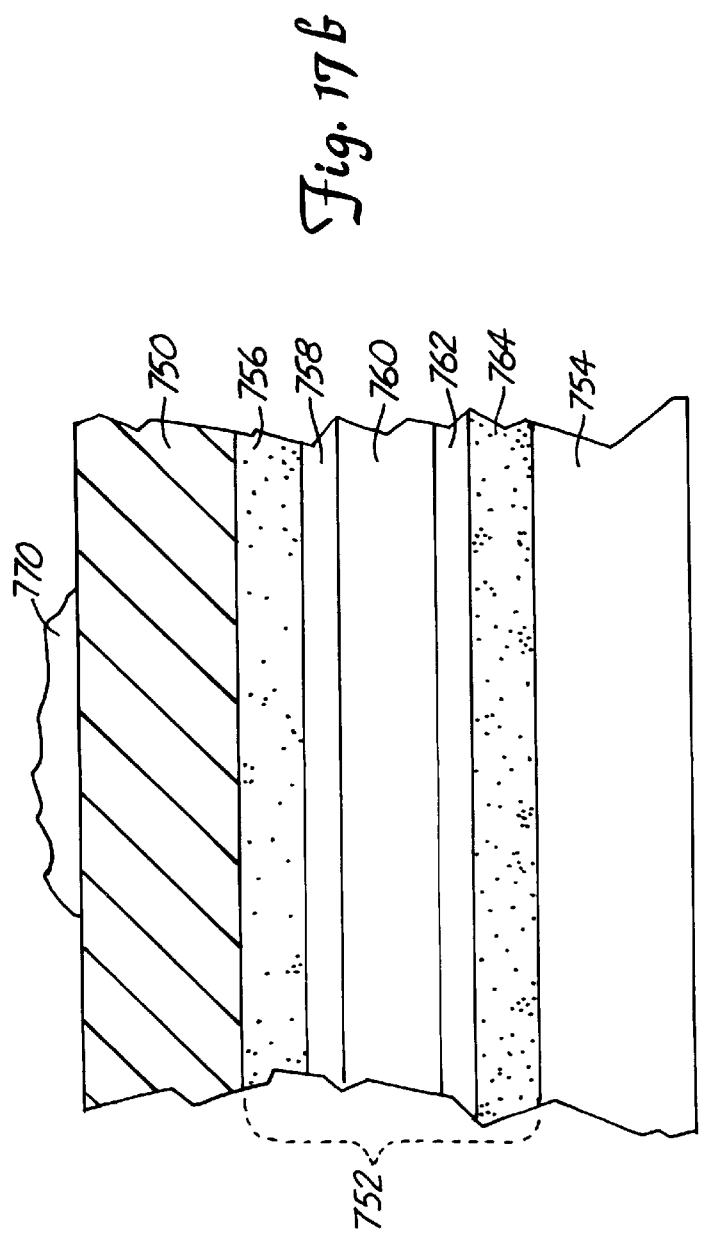
FIG. 17b is an enlarged detailed view of the contaminant detection system illustrated in FIG. 17a, taken along line 17b—17b.

Referring now to FIGS. 17A, 17B an alternative embodiment in accordance with the present invention includes an outer protective skin 750 which protects a PVDF thin sensor 752 which is disposed over an airfoil 754. The PVDF thin sensor 752 is comprised of a top, double sided adhesive layer 756, a sensor electrode 758, a PVDF film 760, a bottom sensor electrode 762, and a bottom, double sided adhesive layer 764. The layers 750, 756, 758, 760, 762 and 764 effectively create a mechanical system consisting of mass, springs, and dampers. By measuring the complex impedance required to stimulate the mechanical system as a function of frequency, it is possible to classify the contaminant 770 disposed on the protective outer layer 750. It is also possible to determine the quantity of contaminant.

Referring now to FIG. 18, an alternative embodiment of a contaminant detection system 800 in accordance with the present invention includes a contaminant detection sheet or strip 816 which is disposed on top of an airfoil 818. An ultrasonic probe 810 transmits and receives guided waves (illustrated by lines 814) through a coupler 812 and is controlled via a line 820. Sheet 816 serves as a wave guide for both outgoing and reflected energy. A plurality of polyvinylidene fluoride (hereinafter, "PVDF") film transducers 822–826 are disposed on the non-exposed side of sheet 816 to capture energy leakage from contaminants 828 on top of sheet 816. In addition to the attenuation and other characteristics discussed hereinbefore that are utilized to obtain contaminant information, the PVDF transducers provide contaminant location information.

It is to be noted that an exteriorly disposed contaminant sheet isn't necessary for the embodiment illustrated in FIG. 18. In other words, sheet 816 could also represent the skin itself. Structure 818 would then represent some other underlying airfoil structure. Transducers 822–826 would therefore be placed directly under the skin.

Figure 19:
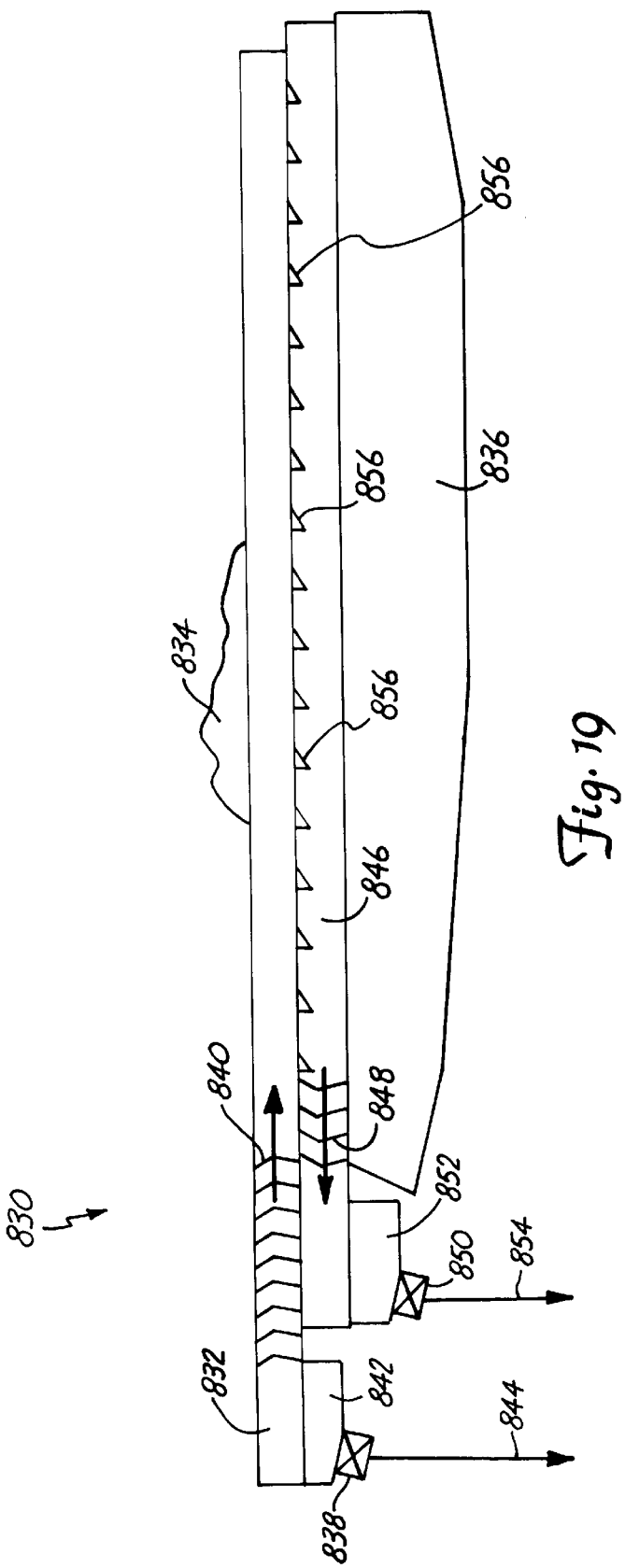
FIG. 19 is a side view of an alternative embodiment of a contaminant detection system in accordance with the present invention.

Referring now to FIG. 19, an alternative embodiment of a contaminant detection system 830 in accordance with the present invention includes a contaminant collection sheet or strip 832 which collects contaminants 834 and is disposed over an airfoil 836. An ultrasonic probe 838 transmits guided waves (illustrated by lines 840) through a coupler 842 and is controlled via a line 844. Sheet 832 serves as a waveguide for outgoing energy. A second sheet or strip 846 is disposed between the collection sheet 832 and the airfoil 836. Sheet 846 serves as a wave guide for reflected energy (illustrated by lines 848). The reflected energy is received by a receiving transducer 850 through a coupler 852. The electrical receive signal is provided on a line 854. A plurality of slits 856 are provided in sheet 846 for reversing the energy leakage and reflection from contaminants 834 and returning the energy to transducer 850. In addition to the attenuation and other characteristics discussed hereinbefore that are utilized to obtain contaminant information, the slits 856 provide contaminant location information.

It is to be noted that an exteriorly disposed contaminant sheet isn't necessary for the return signal for embodiment illustrated in FIG. 19. In other words, sheet 846 could also represent the skin itself. Structure 836 would then represent some other underlying airfoil structure. Slits 856 therefore be made in the skin itself.

Referring now to FIG. 20, wherein a graph illustrates a typical amplitude versus time profile for a contaminant detection system in accordance with those illustrated in FIGS. 18 and 19 hereinbefore. Line 860 represents a curve expected by an uncontaminated outer sheet. Line 862 represents a curve from a contaminated outer sheet. As can be seen, the amplitude of the received signal drops at points 864, 866. Since group velocity of the particular transmission mode is known, the location of the contaminants at points 864, 866 can be determined from the time at which the amplitude drop occurs.

Although the invention has been shown and described with exemplary embodiments thereof, it should be understood by those skilled in the art that the foregoing and various other changes, omissions and additions may be made therein and thereto without departing from the spirit and scope of the invention.

We claim:

1. A method of detecting contaminants on a skin exposed to the environment comprising the steps of:

transmitting a guided wave through the skin at a non-perpendicular incident angle with respect to the skin, wherein the wave travels at a substantially constant phase velocity corresponding to multiple resonances through the skin;

receiving the wave transmitted through the skin and providing a received signal indicative thereof, wherein the received signal has a frequency signature; and extracting features from the frequency signature of said received signal for classifying contaminants on the skin.

2. A method of detecting contaminants on a skin in accordance with claim 1, wherein said extracting step extracts amplitude features from said received signal.

3. A method of detecting contaminants on a skin in accordance with claim 1, further comprising the step of comparing said extracted features of said received signal with said transmitted guided wave.

4. A method of detecting contaminants on a skin in accordance with claim 1, wherein said transmitting and receiving steps are done utilizing different transducers.

5. A method of detecting contaminants on a skin in accordance with claim 1, wherein said transmitting and receiving steps are done utilizing a single transducer.

6. A method of detecting contaminants on a skin in accordance with claim 1, further comprising the step of disposing a contaminant detection sheet onto the skin and wherein said guided waves are transmitted and received through said contaminant detection sheet.

7. A method of detecting contaminants on a skin in accordance with claim 1, further comprising the steps of repeating said transmitting, receiving and extracting steps a multiplicity of times.

8. A method of detecting contaminants on a skin in accordance with claim 1, further comprising the step of comparing said received signal with a predetermined test signal.

9. The method of claim 1 further comprising the step of sweeping the transmitted guided wave over a predetermined frequency range.

10. The method of claim 9 wherein said predetermined frequency range is 0.2–20 MHz.

11. An apparatus for detecting contaminants on a skin exposed to the environment comprising:

a transmitter for transmitting a guided wave through the skin at a non-perpendicular incident angle with respect to the skin, such that the guided wave travels at a substantially constant phase velocity corresponding to multiple resonances through the skin;

a receiver for receiving said guided wave transmitted through the skin;

means for providing a received signal indicative of the received wave, wherein the received wave has a frequency signature; and a signal processor for extracting features from the frequency signature of said received signal for classifying contaminants on the skin.

12. An apparatus for detecting contaminants on a skin in accordance with claim 11, wherein said signal processor extracts amplitude features from said received signal.

13. An apparatus for detecting contaminants on a skin in accordance with claim 11, wherein said signal processor compares said extracted features of said received signal with said transmitted guided wave.

14. An apparatus for detecting contaminants on a skin in accordance with claim 11, wherein said transmitter and receiver are different transducers.

15. An apparatus for detecting contaminants on a skin in accordance with claim 11, wherein said transmitter and receiver are single transducers.

16. An apparatus for detecting contaminants on a skin in accordance with claim 11, further comprising a contaminant detection sheet disposed on the skin and wherein said guided waves are transmitted and received through said contaminant detection sheet.

17. An apparatus for detecting contaminants on a skin in accordance with claim 11, wherein said signal processor compares said received signal with a predetermined test signal.

18. The apparatus of claim 11 wherein the transmitter transmits the guided wave over a predetermined frequency range.

19. The transmitter of claim 18 wherein said predetermined frequency range is 0.2–20 MHz.

\* \* \* \* \*